(12) United States Patent (10) Patent No.: US 12,369,819 B2
Vleugels et al. (45) Date of Patent: Jul. 29, 2025

(54) MULTI-SENSOR GESTURE-BASED OPERATION OF A MEDICATION DELIVERY SYSTEM

(71) Applicant: MEDTRONIC MINIMED, INC., Northridge, CA (US)

(72) Inventors: Katelijn Vleugels, San Carlos, CA (US); Harry J. Eakins, San Jose, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 195 days.

(21) Appl. No.: 17/119,007

(22) Filed: Dec. 11, 2020

(65) Prior Publication Data

US 2021/0177306 A1 Jun. 17, 2021

Related U.S. Application Data

(60) Provisional application No. 62/948,015, filed on Dec. 13, 2019.

(51) Int. Cl.
*A61B 5/11* (2006.01)
*A61B 5/00* (2006.01)
(Continued)

(52) U.S. Cl.
CPC .......... *A61B 5/1112* (2013.01); *A61B 5/0004* (2013.01); *A61B 5/0022* (2013.01);
(Continued)

(58) Field of Classification Search
CPC ... A61B 5/1112; A61B 5/0004; A61B 5/0022; A61B 5/6815; A61B 5/7246;
(Continued)

(56) References Cited

U.S. PATENT DOCUMENTS

| 4,562,751 A | 1/1986 | Nason et al. |
|---|---|---|
| 4,685,903 A | 8/1987 | Cable et al. |

(Continued)

OTHER PUBLICATIONS

U.S. Non-Final office Action dated Jan. 12, 2023 in U.S. Appl. No. 17/118,105.
(Continued)

*Primary Examiner* — Tse W Chen
*Assistant Examiner* — Joseph A Tombers
(74) *Attorney, Agent, or Firm* — Weaver Austin Villeneuve & Sampson LLP

(57) ABSTRACT

Gesture-informed patient management systems and related medical devices and operating methods are provided. A method of operating a medical device capable of influencing a physiological condition of a patient involves obtaining first sensor measurement data from a sensing arrangement associated with a first location on a body of the patient and capable of detecting physical movement by the patient, obtaining second sensor measurement data from a second sensing arrangement having a second location different from the first location, predicting an occurrence of an event based at least in part on the first sensor measurement data in a manner that is influenced by the second sensor measurement data, resulting in a predicted occurrence of the event, and automatically configuring operation of the medical device to influence the physiological condition of the patient in a manner that is influenced by the predicted occurrence of the event.

19 Claims, 10 Drawing Sheets

(51) Int. Cl.
*A61M 5/172* (2006.01)
*G06F 3/01* (2006.01)

(52) U.S. Cl.
CPC .......... *A61B 5/6815* (2013.01); *A61B 5/7246* (2013.01); *A61B 5/7275* (2013.01); *A61M 5/172* (2013.01); *G06F 3/017* (2013.01); *A61M 2205/18* (2013.01); *A61M 2205/502* (2013.01); *A61M 2205/52* (2013.01); *A61M 2205/587* (2013.01); *A61M 2230/201* (2013.01); *A61M 2230/63* (2013.01)

(58) Field of Classification Search
CPC ... A61B 5/7275; A61B 5/14532; A61B 5/681; A61M 5/172; A61M 2205/18; A61M 2205/502; A61M 2205/52; A61M 2205/587; A61M 2230/201; A61M 2230/63; A61M 5/14244; A61M 5/24; A61M 2205/3553; A61M 2209/01; A61M 5/1723; G06F 3/017; G06V 40/23
See application file for complete search history.

(56) References Cited

U.S. PATENT DOCUMENTS

| | | | |
|---|---|---|---|
| 4,755,173 | A | 7/1988 | Konopka et al. |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,283,763 | B1 | 9/2001 | Matsuzaki et al. |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Larsen et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 9,207,767 | B2 | 12/2015 | Bell et al. |
| 9,517,109 | B2 | 12/2016 | Maeda et al. |
| 9,878,097 | B2 | 1/2018 | Estes |
| 9,943,372 | B2 | 4/2018 | Sholev et al. |
| 10,383,694 | B1 | 8/2019 | Venkataraman et al. |
| 11,037,070 | B2 | 6/2021 | Salganicoff et al. |
| 11,177,025 | B2 | 11/2021 | Bettencourt-Silva et al. |
| 11,191,899 | B2 | 12/2021 | Roy et al. |
| 11,197,949 | B2 | 12/2021 | Dang et al. |
| 11,241,537 | B2 | 2/2022 | Jiang et al. |
| 11,344,235 | B2 | 5/2022 | Nogueira et al. |
| 11,344,674 | B2 | 5/2022 | Palerm |
| 11,450,048 | B2 | 9/2022 | Marchand |
| 11,488,700 | B2 | 11/2022 | Monirabbasi et al. |
| 11,672,621 | B2 | 6/2023 | Hulford et al. |
| 2002/0041327 | A1 | 4/2002 | Hildreth et al. |
| 2007/0123819 | A1 | 5/2007 | Mernoe et al. |
| 2008/0013826 | A1 | 1/2008 | Hillis et al. |
| 2009/0027337 | A1 | 1/2009 | Hildreth |
| 2010/0160861 | A1 | 6/2010 | Causey, III et al. |
| 2010/0280988 | A1 | 11/2010 | Underkoffler et al. |
| 2011/0137141 | A1* | 6/2011 | Razoumov ........... A61B 5/0002 600/324 |
| 2011/0152882 | A1 | 6/2011 | Wenderow et al. |
| 2011/0187746 | A1 | 8/2011 | Suto et al. |
| 2012/0019369 | A1 | 1/2012 | Taskinen et al. |
| 2012/0197196 | A1 | 8/2012 | Halbert et al. |
| 2015/0037775 | A1 | 2/2015 | Ottensmeyer et al. |
| 2015/0119651 | A1* | 4/2015 | Grubis ................. A61B 5/01 128/202.13 |
| 2015/0126963 | A1 | 5/2015 | Despa et al. |
| 2015/0289823 | A1* | 10/2015 | Rack-Gomer ......... A61B 5/746 600/365 |
| 2016/0030683 | A1 | 2/2016 | Taylor et al. |
| 2016/0109960 | A1 | 4/2016 | Steinle et al. |
| 2016/0378939 | A1 | 12/2016 | Baumberger et al. |
| 2017/0091259 | A1 | 3/2017 | Curran |

(56) References Cited

U.S. PATENT DOCUMENTS

| | | |
|---|---|---|
| 2017/0220772 A1* | 8/2017 | Vleugels ............. A61B 5/0022 |
| 2017/0262169 A1 | 9/2017 | Kim et al. |
| 2017/0360403 A1 | 12/2017 | Rothberg et al. |
| 2018/0174675 A1 | 6/2018 | Roy et al. |
| 2018/0185578 A1 | 7/2018 | Monirabbasi et al. |
| 2018/0268110 A1 | 9/2018 | Huynh |
| 2018/0353698 A1 | 12/2018 | Saint et al. |
| 2019/0117809 A1 | 4/2019 | Katz |
| 2019/0252079 A1* | 8/2019 | Constantin ........... A61B 5/0024 |
| 2019/0380792 A1 | 12/2019 | Poltaretskyi et al. |
| 2020/0054406 A1 | 2/2020 | Hanuschik et al. |
| 2020/0104039 A1 | 4/2020 | Robertson et al. |
| 2020/0111578 A1 | 4/2020 | Koblick et al. |
| 2020/0135320 A1 | 4/2020 | Vleugels |
| 2020/0289373 A1 | 9/2020 | Vleugels |
| 2021/0050085 A1 | 2/2021 | Hayter et al. |
| 2021/0100951 A1* | 4/2021 | Chase ................... A61B 5/1118 |
| 2021/0178063 A1 | 6/2021 | Parikh et al. |
| 2021/0183489 A1 | 6/2021 | Monirabbasi et al. |
| 2021/0186632 A1 | 6/2021 | Quaid et al. |
| 2021/0327304 A1 | 10/2021 | Buras et al. |
| 2023/0005589 A1 | 1/2023 | Monirabbasi et al. |

OTHER PUBLICATIONS

U.S Final Office Action dated Feb. 18, 2022, in U.S. Appl. No. 17/118,984.
U.S. Final Office Action dated May 8, 2024 in U.S. Appl. No. 17/943,491.
U.S Non-Final Office Action dated Aug. 9, 2021, in U.S. Appl. No. 17/118,984.
U.S. Non-Final Office Action dated Dec. 20, 2023 in U.S. Appl. No. 17/943,491.
U.S Notice of Allowance dated Jun. 13, 2022 in U.S. Appl. No. 17/118,984.
U.S. Advisory Action dated Aug. 5, 2024 in U.S. Appl. No. 17/943,491.
U.S. Non-Final Office Action dated Nov. 19, 2024 in U.S. Appl. No. 17/943,491.

* cited by examiner

MULTI-SENSOR GESTURE-BASED OPERATION OF A MEDICATION DELIVERY SYSTEM

CROSS-REFERENCE TO RELATED APPLICATION

This application claims the benefit of U.S. Provisional Patent Application Ser. No. 62/948,015, which was filed on Dec. 13, 2019, and is incorporated by reference herein in its entirety.

TECHNICAL FIELD

The present technology is generally related to the control, operation, and adjustment of a medication delivery system in response to patient lifestyle events or activities detected using a gesture-based physical behavior detection system.

BACKGROUND

Medical therapy delivery systems, such as fluid infusion devices, are relatively well known in the medical arts for use in delivering or dispensing an agent, such as insulin or another prescribed medication, to a patient. A typical medication infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

Regulating blood glucose level is complicated by variations in the response time for the type of insulin being used along with each patient's individual insulin response. Furthermore, a patient's daily activities and experiences may cause that patient's insulin response to vary throughout the course of a day or from one day to the next. Thus, it is desirable to account for the anticipated variations or fluctuations in the patient's insulin response caused by the patient's activities or other condition(s) experienced by the patient. Managing a diabetic's blood glucose level is also complicated by the patient's consumption of meals or carbohydrates. Often, a patient manually administers a bolus of insulin at or around meal time to mitigate postprandial hyperglycemia. While undesirably increasing the burden on the patient for managing his or her therapy, manual errors such as miscounting carbohydrates or failing to initiate a bolus in a timely manner can also reduce the therapy effectiveness. Accordingly, there is a need to facilitate improved glucose control and reduce patient workload.

BRIEF SUMMARY

The subject matter of this disclosure generally relates to gesture-informed patient management systems and related medical devices and operating methods for controlling or adjusting delivery of a fluid or other medicament, such as insulin, in response to patient lifestyle events or activities detected using a gesture-based physical behavior detection system.

In one embodiment, a method of operating a medical device capable of influencing a physiological condition of a patient is provided. The method involves obtaining, by a control system associated with the medical device, first sensor measurement data from a sensing arrangement capable of detecting physical movement by the patient, wherein the sensing arrangement is associated with a first location on a body of the patient, obtaining, by the control system, second sensor measurement data from a second sensing arrangement having a second location different from the first location, predicting, by the control system, an occurrence of an event based at least in part on the first sensor measurement data in a manner that is influenced by the second sensor measurement data, resulting in a predicted occurrence of the event, and automatically configuring operation of the medical device to influence the physiological condition of the patient in a manner that is influenced by the predicted occurrence of the event.

In another embodiment, at least one non-transitory computer readable medium having stored thereon program code instructions is provided. The program code instructions are configurable to cause at least one processor to obtain first sensor measurement data from a primary sensing arrangement capable of detecting physical movement by a patient, obtain second sensor measurement data from a secondary sensing arrangement having a different location than the primary sensing arrangement, predict an occurrence of an event based at least in part on the first sensor measurement data in a manner that is influenced by the second sensor measurement data, resulting in a predicted occurrence of the event, and automatically configure operation of a medical device to influence a physiological condition of the patient in a manner that is influenced by the predicted occurrence of the event.

In yet another embodiment, a system is provided that includes a medical device that regulates delivery of fluid to a patient, a primary sensor unit associated with a location on a body of the patient to provide first sensor measurement data corresponding to a physical movement by the patient, a secondary sensor unit to provide second sensor measurement data, and at least one controller that controls operation of the medical device. The at least one controller is configured to predict an occurrence of an event based at least in part on the first sensor measurement data in a manner that is influenced by the second sensor measurement data and automatically configure operation of the medical device to deliver the fluid in a manner that is influenced by the occurrence of the event.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
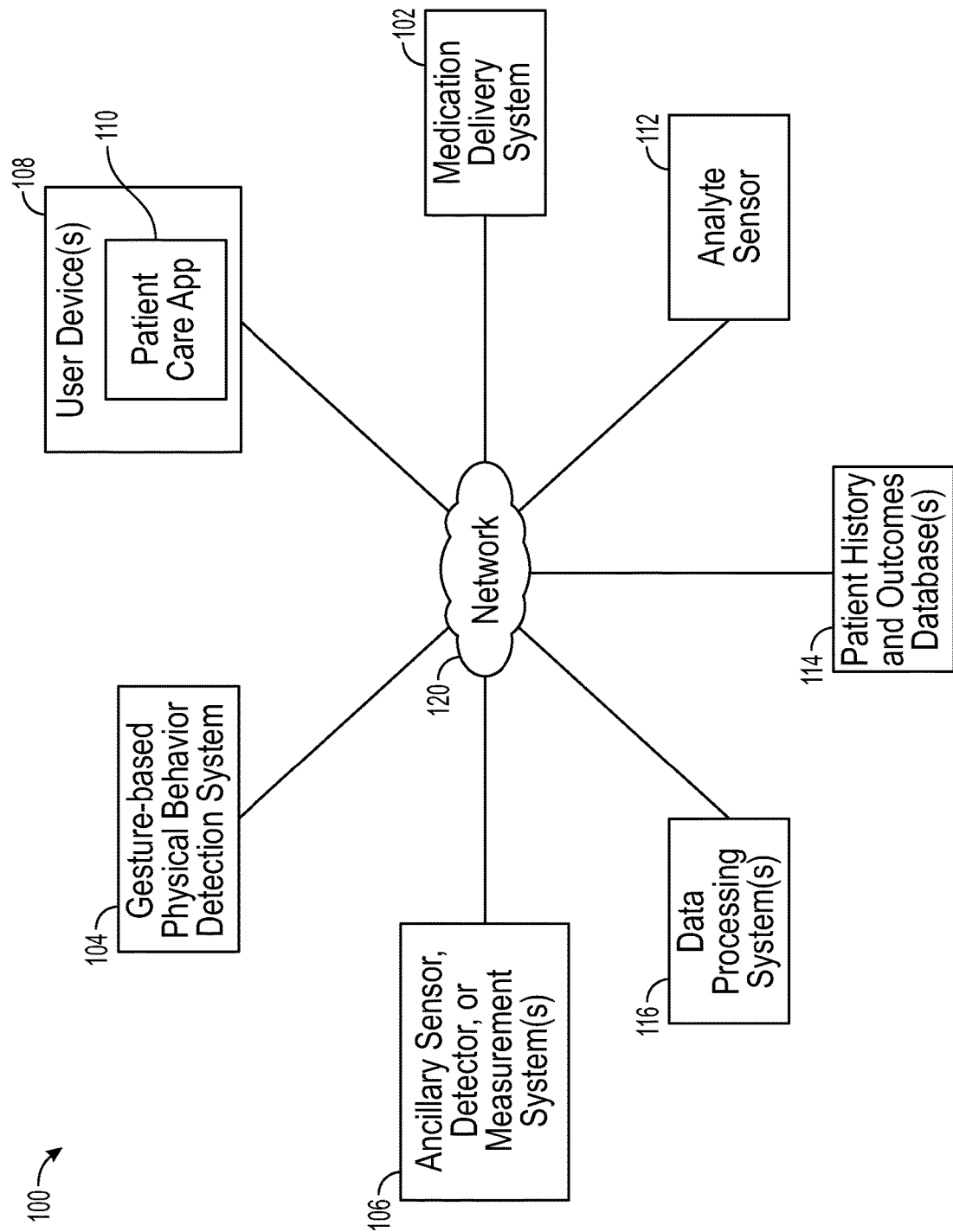
FIG. 1 is a simplified block diagram representation of an exemplary embodiment of a system that includes a medication delivery system that responds to changes in patient activity as indicated by the output of a gesture-based physical behavior detection system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more exemplary embodiments, the subject matter described herein is implemented in connection with a portable electronic medical device. Although many different applications are possible, for purposes of explanation, the following description may focus on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Program code instructions may be configurable to be executed by one or more processors, such as one or more digital signal processors (DSPs), general purpose microprocessors, controllers, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

FIG. 1 is a simplified block diagram representation of an exemplary embodiment of a system 100 that regulates operation of a medication delivery system 102 or other medical device to thereby regulate a physiological condition of a patient user in response to events or other activities (e.g., eating, sleeping, exercise, and/or working, and/or the like) detected based on physical movements by the patient. In certain embodiments, the medication delivery system 102 responds to the patient's behavior as indicated by the output of a gesture-based physical behavior detection system 104 and/or the output of at least one ancillary sensor, detector, or measurement system 106 (hereinafter referred to as ancillary system(s) 106). Certain embodiments of the system 100 include, without limitation: the medication delivery system 102 (or device) that regulates delivery of medication to a patient user; at least one gesture-based physical behavior detection system 104 that monitors user behavior and/or status to obtain gesture data that indicates user activity events or behavior; at least one ancillary system 106; at least one user device 108 that includes or cooperates with a suitably written and configured patient care application 110; an analyte sensor 112 to measure a physiological characteristic of the user, such that sensor data obtained from the analyte sensor 112 can be used to control, regulate, or otherwise influence the operation of the medication delivery system 102; and at least one patient history and outcomes database 114. In accordance with certain cloud-implemented embodiments, the system includes at least one data processing system 116, which may be in communication with any or all of the other components of the system 100. Other configurations and topologies for the system 100 are also contemplated here, such as a system that includes additional intermediary, interface, or data repeating devices in the data path between a sending device and a receiving device.

At least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

In certain embodiments, at least some of the features or output of the gesture-based physical behavior detection system 104 and/or the ancillary system(s) 106 can be used to influence features, functions, and/or therapy-related operations of the medication delivery system 102. As described in more detail below, the gesture-based physical behavior detection system 104 includes one or more sensors, detectors, measurement devices, and/or readers to automatically detect certain user gestures that correlate to user activities or events (e.g., socializing, eating, sleeping, exercising, or watching television). The gesture-based physical behavior detection system 104 may communicate gesture data to the medication delivery system 102, the user device 108, and/or the data processing system 116 for processing in an appropriate manner for use in regulating or controlling certain functions of the medication delivery system 102. For example, the gesture data may be communicated to a user device 108, such that the user device 108 can process the gesture data and inform the user or the medication delivery system 102 as needed (e.g., remotely regulate or control certain functions of the medication delivery system 102). As another example, the gesture-based physical behavior detection system 104 may communicate the gesture data to one or more cloud computing systems or servers (such as a remote data processing system 116) for appropriate processing and handling in the manner described herein.

Similarly, an ancillary system 106 may include one or more sensors, detectors, measurement devices, and/or readers that obtain ancillary user status data that correlates to events or activities by a user. In certain embodiments, an ancillary system 106 may include, cooperate with, or be realized as any of the following, without limitation: a heartrate monitor linked to the user; a blood pressure monitor linked to the user; a respiratory rate monitor linked to the user; a vital signs monitor linked to the user; a microphone; a thermometer (for the user's body temperature and/or the environmental temperature); a sweat detector linked to the user; an activity tracker linked to the user; a global positioning system (GPS); a clock, calendar, or appointment application linked to the user; a pedometer linked to the user; or the like. An ancillary system 106 may be configured and operated to communicate its output (user status data) to one or more components of the system 100 for analysis, processing, and handling in the manner described herein. In certain embodiments, user status data obtained from one or more ancillary systems 106 supplements the gesture data obtained from the gesture-based physical behavior detection system 104, such that user habits, physical behavior, and activity events are accurately and reliably detected.

As described in greater detail below in the context of FIGS. 10-11, in one or more exemplary embodiments, the gesture-based physical behavior detection system 104 utilizes the output of one or more secondary sensing arrangements to augment or otherwise refine the accuracy of gestures detected based on the output of a primary sensing arrangement. For example, the primary sensing arrangement may be realized as the one or more sensors of the gesture-based physical behavior detection system 104 that are embedded in, integrated with, or otherwise associated with a wearable device associated with a patient for monitoring or tracking physical movements of the patient, such as, for example, a smart watch, a wrist band, an activity tracker, or the like.

In some embodiments, the secondary sensing arrangement is duplicative of or redundant to the primary sensing arrangement. For example, the gesture-based physical behavior detection system 104 may employ a smart watch that includes gyroscopes, accelerometers, and other sensors configured to provide a primary sensing arrangement for monitoring or tracking physical movements by the patient's hand and/or wrist of one arm, while the secondary sensing arrangement is realized as another wrist-worn wearable device (e.g., a smart watch, a wrist band, an activity tracker, or the like) that includes counterpart gyroscopes, accelerometers, and other sensors for monitoring or tracking physical movements by the patient's opposing hand and/or wrist. In this regard, in some embodiments, the sensing technology of the secondary sensing arrangement may be substantially the same as the sensing technology utilized by the primary sensing arrangement for monitoring or tracking physical movements.

In other embodiments, the secondary sensing arrangement is different from the primary sensing arrangement, associated with a different part of the patient's body and/or employs different sensing technology. In this regard, it should be appreciated that the subject matter described herein is not limited to any particular type, number, or combination of secondary sensing arrangements, and in practice, the secondary sensing arrangements may be realized using different types of devices, which may include different sensors associated therewith or otherwise leverage different sensing technologies. Moreover, in some embodiments, the secondary sensing arrangement(s) may be worn or otherwise associated with the body of the patient so as to measure or otherwise respond to movements by the patient's body, while in other embodiments, the secondary sensing arrangement may independent of the patient's body or have a fixed location. For example, in some embodiments, the secondary sensing arrangement may have a location that is independent of the patient's body and utilize proximity sensing techniques to provide measurements indicative of a physical movement of the patient without moving or directly measuring the movement.

In some embodiments, the system 100 includes an ancillary system 106 having a secondary sensing arrangement that provides measurement data to the gesture-based physical behavior detection system 104, and the gesture-based physical behavior detection system 104 utilizes the secondary sensing arrangement measurement data to augment gesture detection based on the measurement data output from the primary sensing arrangement. In this regard, the secondary sensing arrangement may be embedded in, integrated with, or otherwise associated with a wearable device associated with a different part or region of the patient's body than the primary sensing arrangement. For example, the secondary sensing arrangement may be a component of an in-ear device (e.g., in-ear headphones or earbuds) or a head-worn device (e.g., smart glasses). As another example, the secondary sensing arrangement may be associated with an electronic device associated with the patient, such as, for example, the patient's mobile phone, headphones or earbuds (with or without a microphone), smart speaker, smart thermometer, Wi-Fi router, or any other user device 108. In yet other embodiments, the secondary sensing arrangement may be associated with one of a patient's medical devices, such as the analyte sensor 112 or a fluid delivery device that is part of the medical delivery system 102. For example, the analyte sensor 112 may be realized as a CGM device that is affixed to or otherwise worn on the patient's upper arm or other location of the body and includes one or more gyroscopes, accelerometers, and/or other sensors for monitoring or tracking physical movements of the respective body part that is different from that associated with the primary sensing arrangement. As another example, a patient's infusion device, smart injection pen, or other fluid delivery device that is carried or worn by the patient may similarly include one or more gyroscopes, accelerometers, and other sensors for monitoring or tracking physical movements associated therewith.

As described in greater detail below, the measurement data output from the secondary sensing arrangement is utilized to augment, enhance, or otherwise improve the accuracy of the prediction or detection of the probable occurrence of an event or activity by a patient based on the primary sensing arrangement measurement data before automatically configuring the medical delivery system 102 to adjust or otherwise influence fluid delivery to regulate a physiological condition of the patient in a manner that is influenced by the predicted occurrence of the event. For example, in some embodiments, correlations between the primary and secondary sensor measurement data may be utilized to assign a higher or lower probability or confidence value to a detected gesture, which, in turn may influence the predicted event occurrence based on that detected gesture. In other embodiments, correlations between the primary and secondary sensor measurement data may also be utilized to recognize or detect performance of a gesture, for example, by imputing both the primary and secondary sensor measurement data into a gesture recognition machine learning model, with the detected gesture output by the model in turn influencing event prediction.

In yet other embodiments, correlations between secondary sensor measurement data and occurrence of an event may be utilized to increase or decrease the probability of detecting occurrence of an event based on a detected gesture, and correspondingly influence the probability or confidence value assigned to the predicted occurrence (or non-occurrence) of an event. For example, in some embodiments, the secondary sensor measurement data may be input to an event prediction model along with detected gesture data derived from the primary sensor measurement data to predict occurrence of an event as a function of the secondary sensor measurement data and primary sensor-based detected gestures. In other embodiments, correlations between secondary sensor measurement data and occurrence of an event may be utilized to assign a probability or confidence value to the occurrence of an event that was predicted or otherwise detected based on detected gestures derived from the primary sensor measurement data. In this regard, it should be appreciated that there are numerous different was secondary sensor measurement data may be utilized to influence detection of gestures based on primary sensor measurement data or the detection or prediction of event occurrence based on such detected gestures, and the subject matter described herein is not limited to any particular combination or manner in which secondary sensor measurement data is utilized to augment gesture detection or event prediction.

Still referring to FIG. 1, the system 100 can support any type of medication delivery system 102 that is compatible with the features and functionality described here. For example, the medication delivery system 102 may be realized as a user-activated or user-actuated fluid delivery device, such as a manual syringe, an injection pen, or the like. As another example, the medication delivery system 102 may be implemented as an electronic device that is operated to regulate the delivery of medication fluid to the user. In certain embodiments, however, the medication delivery system 102 includes or is realized as an insulin infusion device, e.g., a portable patient-worn or patient-carried insulin pump, a smart insulin pen, or the like. In such embodiments, the analyte sensor 112 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Figure 2:
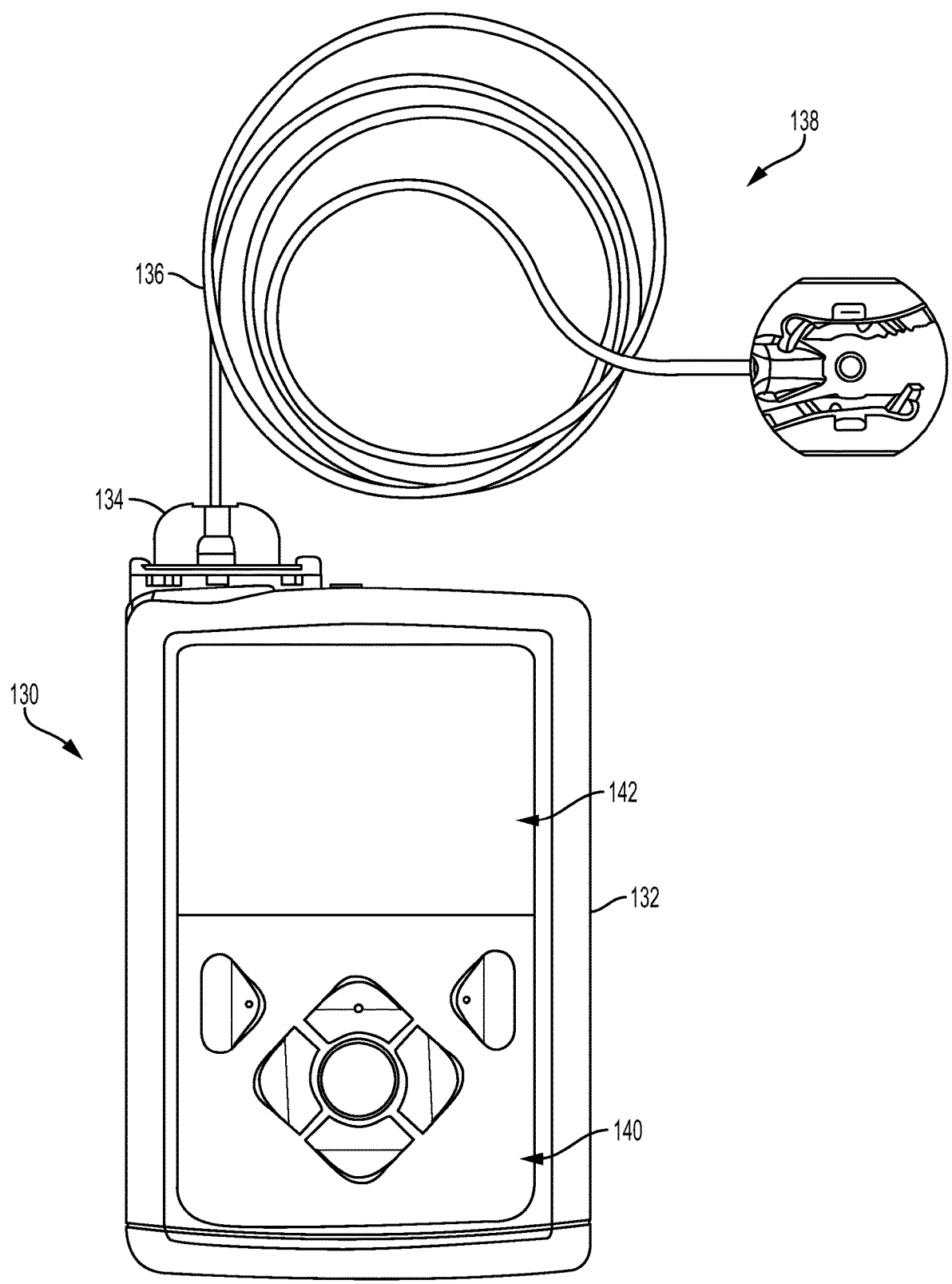
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3:
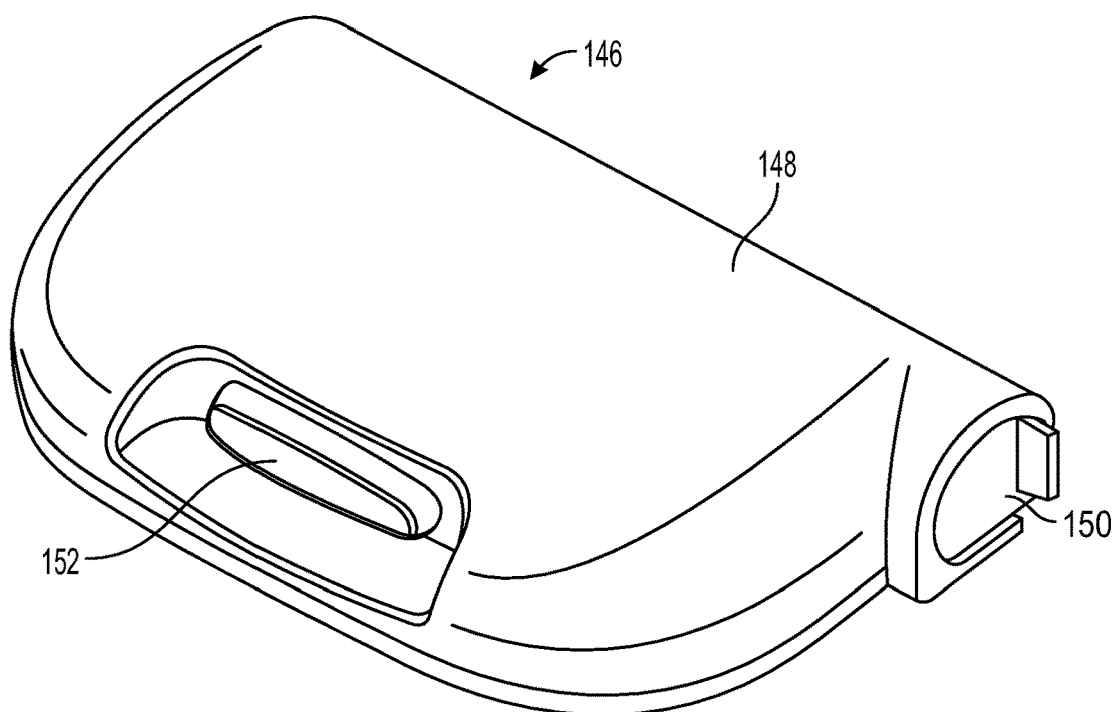
FIG. 3 is a top perspective view of an embodiment of an insulin infusion device implemented as a patch pump device that is suitable for use as the medication delivery system shown in FIG. 1.

FIG. 3 is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3). In such an implementation, the glucose sensor may take the place of the separate analyte sensor 112 shown in FIG. 1. The insulin infusion device 146 includes a housing 148 that serves as a shell for a variety of internal components. FIG. 3 shows the insulin infusion device 146 with a removable fluid cartridge 150 installed and secured therein. The housing 148 is suitably configured to receive, secure, and release the removable fluid cartridge 150. The insulin infusion device 146 includes at least one user interface feature, which can be actuated by the patient as needed. The illustrated embodiment of the fluid infusion device 146 includes a button 152 that is physically actuated. The button 152 can be a multipurpose user interface if so desired to make it easier for the user to operate the fluid infusion device 146. In this regard, the button 152 can be used in connection with one or more of the following functions, without limitation: waking up the processor and/or electronics of the fluid infusion device 146; triggering an insertion mechanism to insert a fluid delivery cannula and/or an analyte sensor into the subcutaneous space or similar region of the user; configuring one or more settings of the fluid infusion device 146; initiating delivery of medication fluid from the fluid cartridge 150; initiating a fluid priming operation; disabling alerts or alarms generated by the fluid infusion device 146; and the like. In lieu of the button 152, the insulin infusion device 146 can employ a slider mechanism, a pin, a lever, a switch, a touch-sensitive element, or the like. In certain embodiments, the insulin infusion device 146 may be configured and controlled to support other features and interactive functions described in more detail below.

Generally, a fluid infusion device (such as an insulin infusion device) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 4:
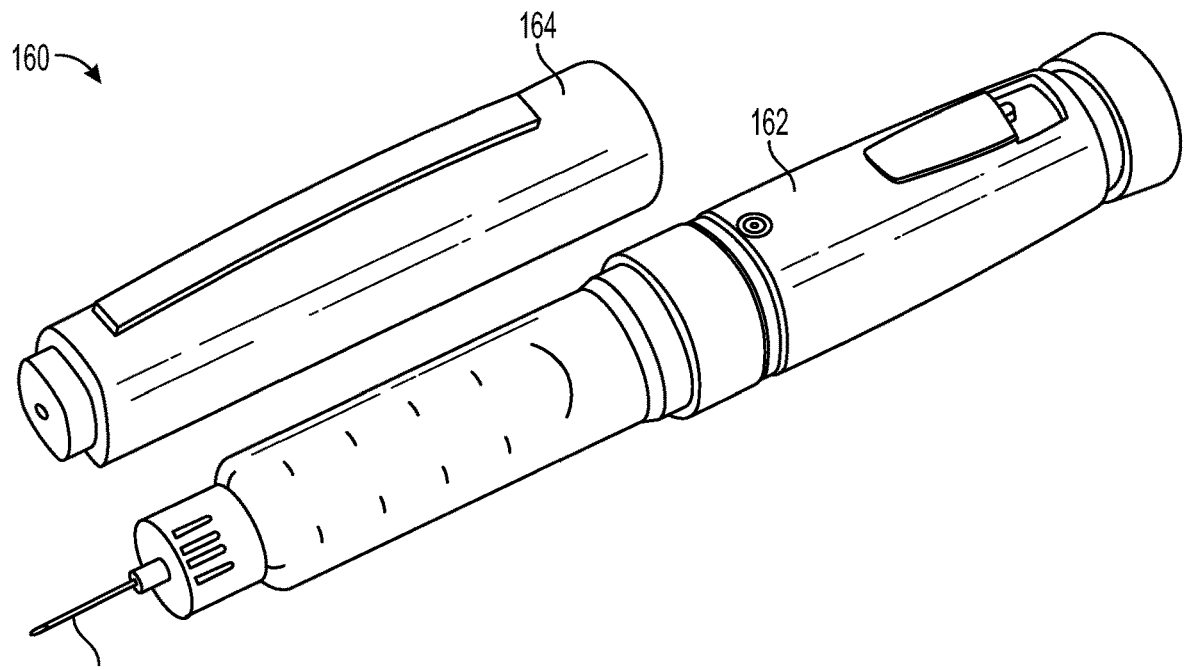
FIG. 4 is a perspective view of an exemplary embodiment of a smart insulin pen that is suitable for use as the medication delivery system shown in FIG. 1.

FIG. 4 is a perspective view of an exemplary embodiment of a smart insulin pen 160 suitable for use as the medication delivery system shown in FIG. 1. The pen 160 includes an injector body 162 and a cap 164. FIG. 4 shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 5:
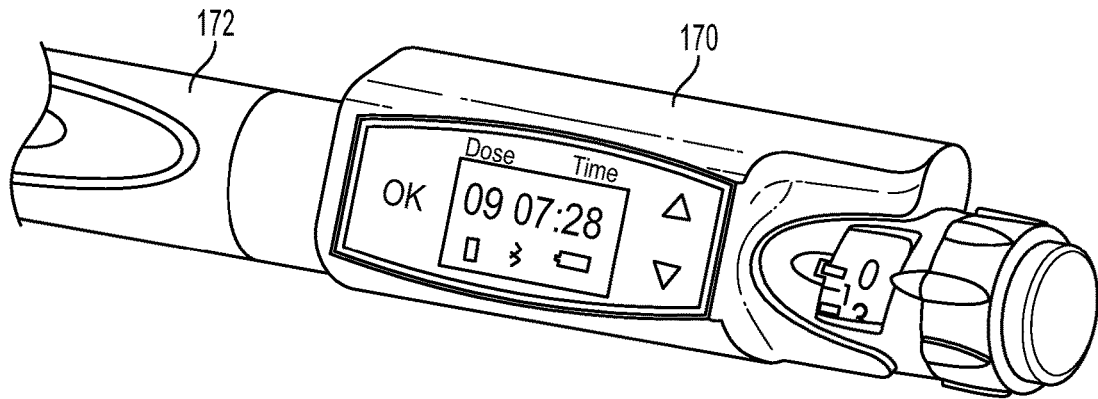
FIG. 5 is a perspective view of an exemplary embodiment of a smart pen accessory that is suitable for use with the medication delivery system shown in FIG. 1.

FIG. 5 is a perspective view of an exemplary embodiment of a smart pen accessory 170 that is suitable for use with the medication delivery system 102 shown in FIG. 1. In particular, the smart pen accessory 170 cooperates with a "non-smart" insulin pen that lacks the intelligence and functionality of a smart insulin pen (as described above). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described above in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

Referring again to FIG. 1, the analyte sensor 112 may communicate sensor data to the medication delivery system 102 for use in regulating or controlling operation of the medication delivery system 102. Alternatively, or additionally, the analyte sensor 112 may communicate sensor data to one or more other components in the system 100, such as, without limitation: a user device 108 (for use with the patient care application 110); a data processing system 116; and/or a patient history and outcomes database 114.

The system 100 can support any number of user devices 108 linked to the particular user or patient. In this regard, a user device 108 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. For the example described here, the medication delivery system 102 and the at least one user device 108 are owned by, operated by, or otherwise linked to a user/patient. Any given user device 108 can host, run, or otherwise execute the patient care application 110. In certain embodiments, for example, the user device 108 is implemented as a smartphone with the patient care application 110 installed thereon. In accordance with another example, the patient care application 110 is implemented in the form of a website or webpage, e.g., a website of a healthcare provider, a website of the manufacturer, supplier, or retailer of the medication delivery system 102, or a website of the manufacturer, supplier, or retailer of the analyte sensor 112. In accordance with another example, the medication delivery system 102 executes the patient care application 110 as a native function.

In certain embodiments, the gesture-based physical behavior detection system 104 and the medication delivery system 102 are implemented as physically distinct and separate components, as depicted in FIG. 1. In such embodiments, the gesture-based physical behavior detection system 104 is external to the medication delivery system 102 and is realized as an ancillary component, relative to the medication delivery system 102. In accordance with alternative embodiments, however, the medication delivery system 102 and the gesture-based physical behavior detection system 104 can be combined into a single hardware component or provided as a set of attached hardware devices. For example, the medication delivery system 102 may include the gesture-based physical behavior detection system 104 or integrate the functionality of the detection system 104. Similarly, the analyte sensor 112 can be incorporated with the medication delivery system 102 or the gesture-based physical behavior detection system 104. These and other arrangements, deployments, and topologies of the system 100 are contemplated by this disclosure.

The at least one patient history and outcomes database 114 includes historical data related to the user's physical condition, physiological response to the medication regulated by the medication delivery system 102, activity patterns or related information, eating patterns and habits, work habits, and the like. In accordance with embodiments where the medication delivery system 102 is an insulin infusion device and the analyte sensor 112 is a glucose meter, sensor, or monitor, the database 114 can maintain any of the following, without limitation: historical glucose data and corresponding date/time stamp information; insulin delivery and dosage information; user-entered stress markers or indicators; gesture data (provided by the gesture-based physical behavior detection system 104) and corresponding date/time stamp information; ancillary user status data (provided by one or more ancillary systems 106) and corresponding date/time stamp data; diet or food intake history for the user; and any other information that may be generated by or used by the system 100 for purposes of controlling the operation of the medication delivery system 102. In certain embodiments, the at least one patient history and outcomes database 114 can receive and maintain training data that is utilized to train, configure, and initialize the system 100 based on historical user behavior, physiological state, operation of the medication delivery system 102, and user-identified activity events.

A patient history and outcomes database 114 may reside at a user device 108, at the medication delivery system 102, at a data processing system 116, or at any network-accessible location (e.g., a cloud-based database or server system). In certain embodiments, a patient history and outcomes database 114 may be included with the patient care application 110. The patient history and outcomes database 114 enables the system 100 to generate recommendations, warnings, and guidance for the user and/or to regulate the manner in which the medication delivery system 102 functions to administer therapy to the user, based on detected user activity.

Figure 6:
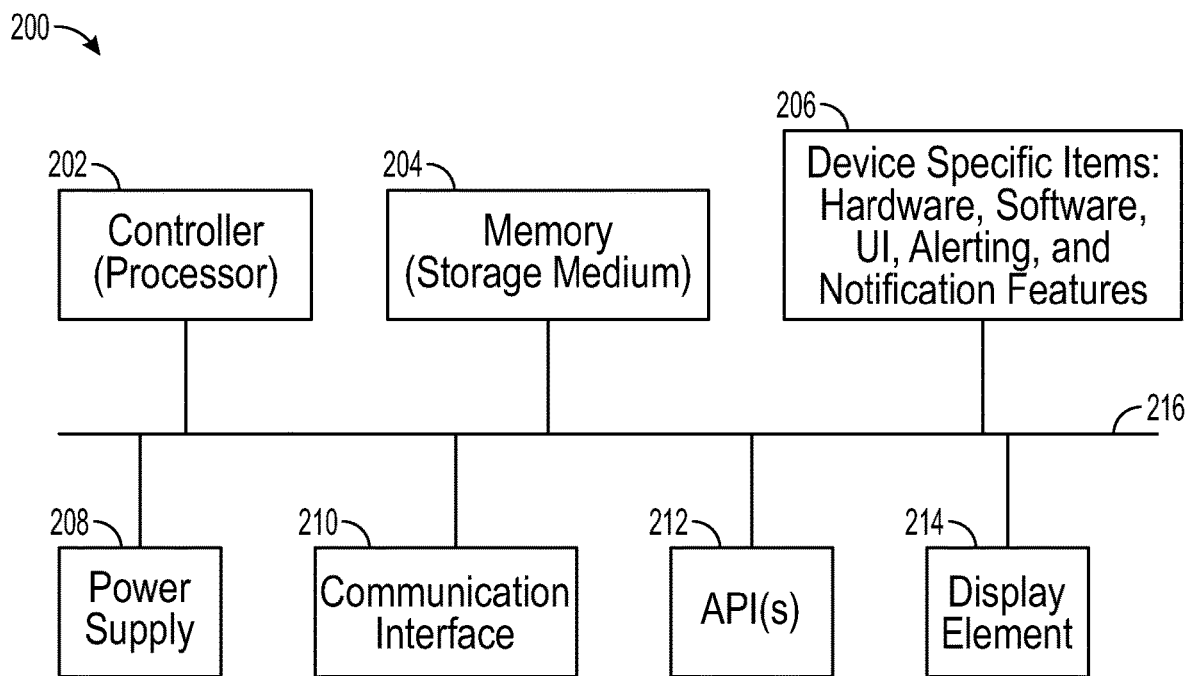
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 200 that is suitable for deployment in the system 100 shown in FIG. 1.

The illustrated embodiment of the device 200 is intended to be a high-level and generic representation of one suitable platform. In this regard, any computer-based or processor-based component of the system 100 can utilize the architecture of the device 200. The illustrated embodiment of the device 200 generally includes, without limitation: at least one controller (or processor) 202; a suitable amount of memory 204 that is associated with the at least one controller 202; device-specific items 206 (including, without limitation: hardware, software, firmware, user interface (UI), alerting, and notification features); a power supply 208 such as a disposable or rechargeable battery; a communication device 210; at least one application programming interface (API) 212; and a display element 214. Of course, an implementation of the device 200 may include additional elements, components, modules, and functionality configured to support various features that are unrelated to the primary subject matter described here. For example, the device 200 may include certain features and elements to support conventional functions that might be related to the particular implementation and deployment of the device 200. In practice, the elements of the device 200 may be coupled together via at least one bus or any suitable interconnection architecture 216.

The at least one controller 202 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 204 can be coupled to the at least one controller 202 such that the at least one controller 202 can read information from, and write information to, the memory 204. In the alternative, the memory 204 may be integral to the at least one controller 202. As an example, the at least one controller 202 and the memory 204 may reside in an ASIC. At least a portion of the memory 204 can be realized as a computer storage medium that is operatively associated with the at least one controller 202, e.g., a tangible, non-transitory computer-readable medium having computer-executable instructions stored thereon. The computer-executable instructions are configurable to be executed by the at least one controller 202 to cause the at least one controller 202 to perform certain tasks, operations, functions, and processes that are specific to the particular embodiment. In this regard, the memory 204 may represent one suitable implementation of such computer-readable media. Alternatively, or additionally, the device 200 could receive and cooperate with computer-readable media (not separately shown) that is realized as a portable or mobile component or platform, e.g., a portable hard drive, a USB flash drive, an optical disc, or the like.

The device-specific items 206 may vary from one embodiment of the device 200 to another. For example, the device-specific items 206 will support: sensor device operations when the device 200 is realized as a sensor device; smartphone features and functionality when the device 200 is realized as a smartphone; activity tracker features and functionality when the device 200 is realized as an activity tracker; smart watch features and functionality when the device 200 is realized as a smart watch; medical device features and functionality when the device is realized as a medical device; etc. In practice, certain portions or aspects of the device-specific items 206 may be implemented in one or more of the other blocks depicted in FIG. 6.

If present, the UI of the device 200 may include or cooperate with various features to allow a user to interact with the device 200. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The UI may include one or more graphical user interface (GUI) control elements that enable a user to manipulate or otherwise interact with an application via the display element 214. The display element 214 and/or the device-specific items 206 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication device 210 facilitates data communication between the device 200 and other components as needed during the operation of the device 200. In the context of this description, the communication device 210 can be employed to transmit or stream device-related control data, patient-related user status (e.g., gesture data or status data), device-related status or operational data, sensor data, calibration data, and the like. It should be appreciated that the particular configuration and functionality of the communication device 210 can vary depending on the hardware platform and specific implementation of the device 200. In practice, an embodiment of the device 200 may support wireless data communication and/or wired data communication, using various data communication protocols. For example, the communication device 210 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication device 210 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 212 supports communication and interactions between software applications and logical components that are associated with operation of the device 200. For example, one or more APIs 212 may be configured to facilitate compatible communication and cooperation with the patient care application 110, and to facilitate receipt and processing of data from sources external to the device 200 (e.g., databases or remote devices and systems).

The display element 214 is suitably configured to enable the device 200 to render and display various screens, recommendation messages, alerts, alarms, notifications, GUIs, GUI control elements, drop down menus, auto-fill fields, text entry fields, message fields, or the like. Of course, the display element 214 may also be utilized for the display of other information during the operation of the device 200, as is well understood. Notably, the specific configuration, operating characteristics, size, resolution, and functionality of the display element 214 can vary depending upon the implementation of the device 200.

Figure 7:
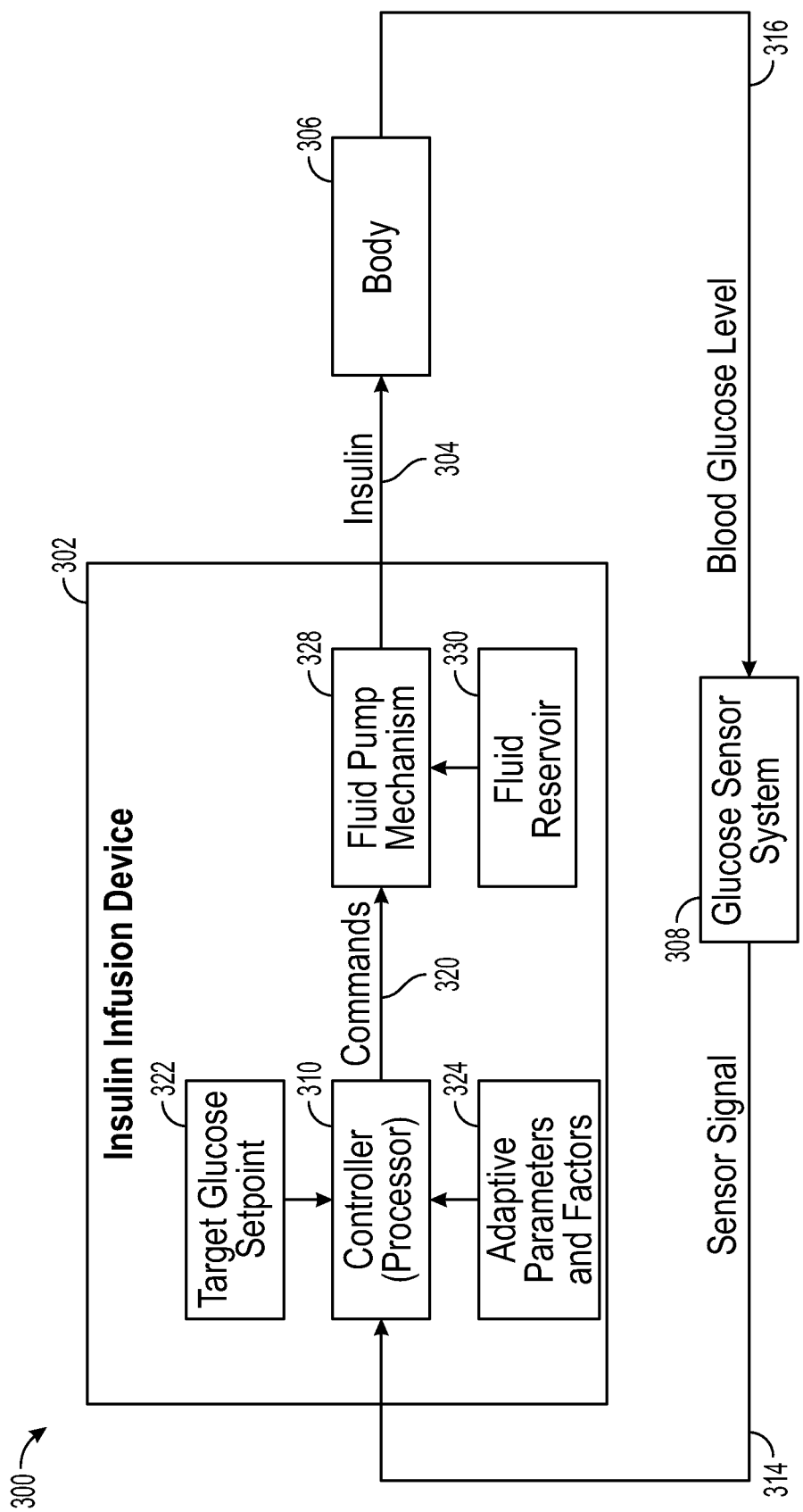
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 300 arranged in accordance with certain embodiments. The system 300 depicted in FIG. 7 functions to regulate the rate of fluid infusion into a body of a user based on feedback from an analyte concentration measurement taken from the body. In particular embodiments, the system 300 is implemented as an automated control system for regulating the rate of insulin infusion into the body of a user based on a glucose concentration measurement taken from the body. The system 300 is designed to model the physiological response of the user to control an insulin infusion device 302 in an appropriate manner to release insulin 304 into the body 306 of the user in a similar concentration profile as would be created by fully functioning human β-cells when responding to changes in blood glucose concentrations in the body. Thus, the system 300 simulates the body's natural insulin response to blood glucose levels and not only makes efficient use of insulin, but also accounts for other bodily functions as well since insulin has both metabolic and mitogenic effects.

Certain embodiments of the system 300 include, without limitation: the insulin infusion device 302; a glucose sensor system 308 (e.g., the analyte sensor 112 shown in FIG. 1); and at least one controller 310, which may be incorporated in the insulin infusion device 302 as shown in FIG. 7. The glucose sensor system 308 generates a sensor signal 314 representative of blood glucose levels 316 in the body 306 and provides the sensor signal 314 to the at least one controller 310. The at least one controller 310 receives the sensor signal 314 and generates commands 320 that regulate the timing and dosage of insulin 304 delivered by the insulin infusion device 302. The commands 320 are generated in response to various factors, variables, settings, and control algorithms utilized by the insulin infusion device 302. For example, the commands 320 (and, therefore, the delivery of insulin 304) can be influenced by a target glucose setpoint value 322 that is maintained and regulated by the insulin infusion device 302. Moreover, the commands 320 (and, therefore, the delivery of insulin 304) can be influenced by any number of adaptive parameters and factors 324. The adaptive parameters and factors 324 may be associated with or used by: a therapy control algorithm of the insulin infusion device 302; a digital twin model of the patient, which can be used to recommend manual insulin dosages; a meal prediction algorithm; a user glucose prediction algorithm; or the like.

Generally, the glucose sensor system 308 includes a continuous glucose sensor, sensor electrical components to provide power to the sensor and generate the sensor signal 314, a sensor communication system to carry the sensor signal 314 to the at least one controller 310, and a sensor system housing for the electrical components and the sensor communication system. As mentioned above with reference to FIG. 6, the glucose sensor system 308 may be implemented as a computer-based or processor-based component having the described configuration and features.

Typically, the at least one controller 310 includes controller electrical components and software to generate commands for the insulin infusion device 302 based on the sensor signal 314, the target glucose setpoint value 322, the adaptive parameters and factors 324, and other user-specific parameters, settings, and factors. The at least one controller 310 may include a controller communication system to receive the sensor signal 314 and issue the commands 320.

Generally, the insulin infusion device 302 includes a fluid pump mechanism 328, a fluid reservoir 330 for the medication (e.g., insulin), and an infusion tube to infuse the insulin 304 into the body 306. In certain embodiments, the insulin infusion device 302 includes an infusion communication system to handle the commands 320 from the at least one controller 310, electrical components and programmed logic to activate the fluid pump mechanism 328 motor according to the commands 320, and a housing to hold the components of the insulin infusion device 302. Accordingly, the fluid pump mechanism 328 receives the commands 320 and delivers the insulin 304 from the fluid reservoir 330 to the body 306 in accordance with the commands 320. It should be appreciated that an embodiment of the insulin infusion device 302 can include additional elements, components, and features that may provide conventional functionality that need not be described herein. Moreover, an embodiment of the insulin infusion device 302 can include alternative elements, components, and features if so desired, as long as the intended and described functionality remains in place. In this regard, as mentioned above with reference to FIG. 6, the insulin infusion device 302 may be implemented as a computer-based or processor-based components having the described configuration and features, including the display element 214 or other device-specific items 206 as described above.

The controller 310 is configured and programmed to regulate the operation of the fluid pump mechanism 328 and other functions of the insulin infusion device 302. The controller 310 controls the fluid pump mechanism 328 to deliver the fluid medication (e.g., insulin) from the fluid reservoir 330 to the body 306. As mentioned above, the controller 310 can be housed in the infusion device housing, wherein the infusion communication system is an electrical trace or a wire that carries the commands 320 from the controller 310 to the fluid pump mechanism 328. In alternative embodiments, the controller 310 can be housed in the sensor system housing, wherein the sensor communication system is an electrical trace or a wire that carries the sensor signal 314 from the sensor electrical components to the at least one controller 310. In accordance with some embodiments, the at least one controller 310 has its own housing or is included in a supplemental or ancillary device. In other embodiments, the at least one controller 310, the insulin infusion device 302, and the glucose sensor system 308 are all located within one common housing.

Referring again to FIG. 1, the gesture-based physical behavior detection system 104 employs at least one sensor to obtain corresponding user-specific sensor data. The obtained user-specific sensor data is processed or analyzed by the gesture-based physical behavior detection system 104 and/or by another suitably configured device or component of the system 100 to determine whether the user's current behavior reflects a significant or measurable change in activity. The obtained user-specific sensor data may also be processed or analyzed to obtain certain activity-related parameters, characteristics, and/or metadata for the user. For example, the obtained user-specific sensor data may identify, include, or indicate any or all of the following, without limitation: timestamp data corresponding to the occurrence of detected events; a type, category, or classification of the detected physical behavior or activity; location data; user posture or position information; etc.

The gesture-based physical behavior detection system 104 may include, cooperate with, or be realized as a motion-based physical behavior detection system, an activity-based physical behavior detection system, an image or video based activity detection system, or the like. In certain embodiments, the detection system 104 may be realized as a unitary "self-contained" wearable system that communicates with one or more other components of the system 100. For example, the detection system 104 can be implemented with at least one wearable device such as an activity monitor device, a smart watch device, a smart bracelet or wristband device, or the like. In some embodiments, the detection system 104 may be realized as at least one portable or wearable device that includes or communicates with one or more external or ancillary sensor devices, units, or components. For example, the detection system 104 can be implemented with a wearable or portable smart device that is linked with one or more external sensors worn or carried by the user. These and other possible deployments of the detection system 104 are contemplated by this disclosure. In this regard, United States patent publication number US 2020/0135320 and United States patent publication number US 2020/0289373 disclose gesture-based physical behavior detection systems that are suitable for use as the detection system 104; the entire content of these United States patent documents is incorporated by reference herein.

Figure 8:
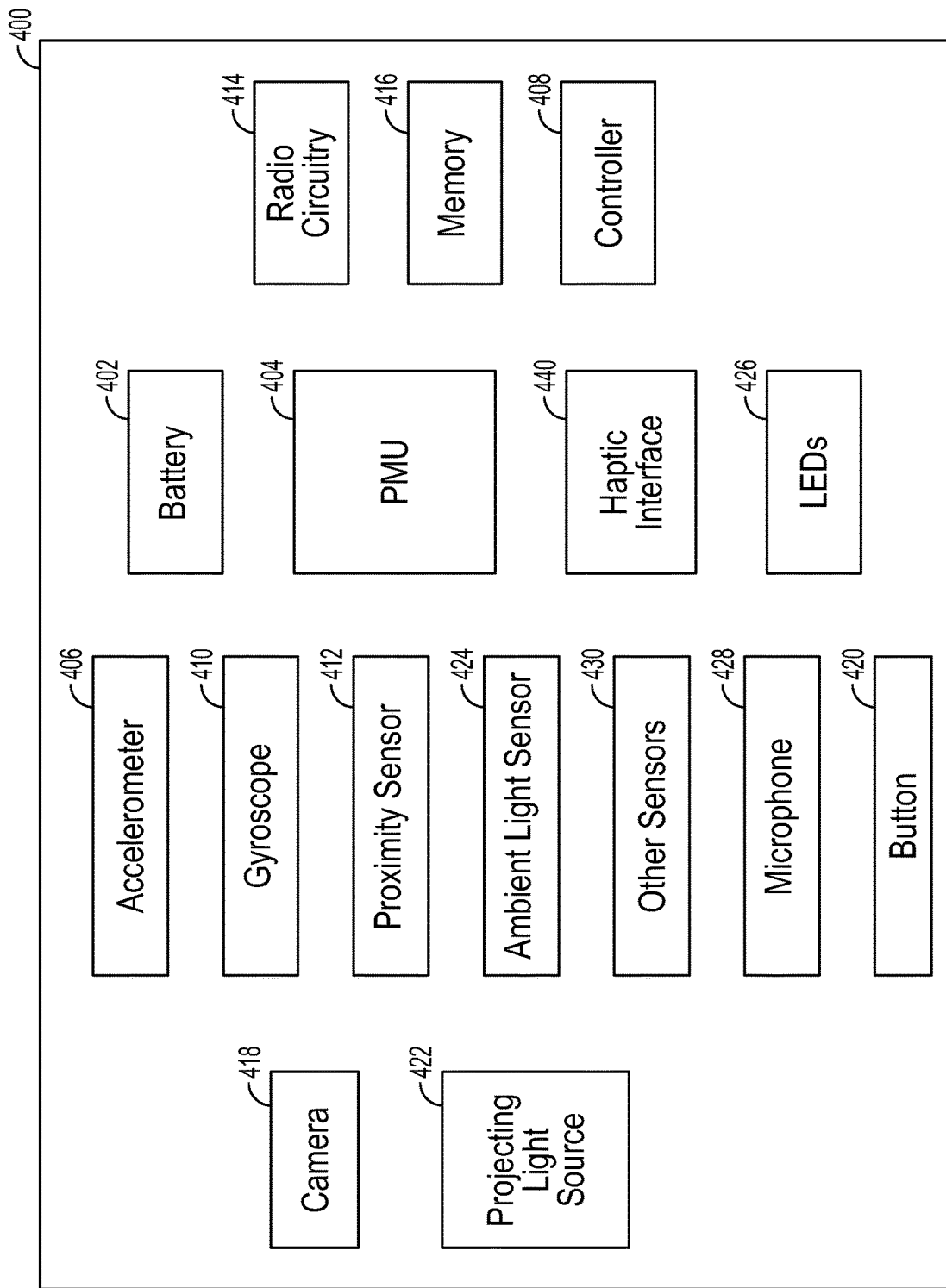
FIG. 8 is a block diagram representation of a gesture-based physical behavior detection system arranged in accordance with certain embodiments.

FIG. 8 is a block diagram representation of a gesture-based physical behavior detection system 400 arranged in accordance with certain embodiments. The system 400 is suitable for use with the system 100 shown FIG. 1. In certain embodiments, the system 400 is deployed as a wearable electronic device in the form factor of a bracelet or wristband that is worn around the wrist or arm of a user's dominant hand. The system 400 may optionally be implemented using a modular design, wherein individual modules include one or more subsets of the disclosed components and overall functionality. The user may choose to add specific modules based on personal preferences and requirements.

The system 400 includes a battery 402 and a power management unit (PMU) 404 to deliver power at the proper supply voltage levels to all electronic circuits and components. The PMU 404 may also include battery-recharging circuitry. The PMU 404 may also include hardware, such as switches, that allows power to specific electronics circuits and components to be cut off when not in use.

When there is no movement-based or gesture-based behavior event in progress, most circuitry and components in the system 400 are switched off to conserve power. Only circuitry and components that are required to detect or help predict the start of a behavior event of interest may remain enabled. For example, if no motion is being detected, all sensor circuits but an accelerometer 406 may be switched off and the accelerometer 406 may be put in a low-power wake-on-motion mode or in another lower power mode that consumes less power and uses less processing resources than its high performance active mode. A controller 408 of the system 400 may also be placed into a low-power mode to conserve power. When motion or a certain motion pattern is detected, the accelerometer 406 and/or the controller 408 may switch into a higher power mode and additional sensors such as, for example, a gyroscope 410 and/or a proximity sensor 412 may also be enabled. When a potential start of a movement-based or gesture-based event is detected, memory variables for storing event-specific parameters, such as gesture types, gesture duration, etc. can be initialized.

In another example, upon detection of user motion, the accelerometer 406 switches into a higher power mode, but other sensors remain switched off until the data from the accelerometer 406 indicates that the start of a behavior event has likely occurred. At that point in time, additional sensors such as the gyroscope 410 and the proximity sensor 412 may be enabled.

In another example, when there is no behavior event in progress, both the accelerometer 406 and gyroscope 410 are enabled but at least one of either the accelerometer 406 or the gyroscope 410 is placed in a lower power mode compared to their regular power mode. For example, the sampling rate may be reduced to conserve power. Similarly, the circuitry required to transfer data from the system 400 to a destination device may be placed in a lower power mode. For example, radio circuitry 414 could be disabled. Similarly, the circuitry required to transfer data from the system 400 may be placed in a lower power mode. For example, the radio circuitry 414 could be disabled until a possible or likely start of a behavior event has been determined. Alternatively, it may remain enabled but in a low power state to maintain the connection between the system 400 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the system 400 has been removed from the wrist or hand, detection that the system 400 is being charged, or the like. Metadata may be generated and collected by the system 400. Alternatively, metadata may be collected by another device that is external to the system 400 and is configured to directly or indirectly exchange information with the system 400. It is also possible that some metadata is generated and collected by the system 400, while other metadata is generated and collected by a device that is external to the system 400. In case some or all of the metadata is generated and collected external to the system 400, the system 400 may periodically or from time to time power up its radio circuitry 414 to retrieve metadata related information from another device.

In certain embodiments, some or all of the sensors may be turned on or placed in a higher power mode if certain metadata indicates that the occurrence of a particular behavior event, such as the user beginning to work, jog, or eat, is likely. Metadata used to make this determination may, among other things, include one or more of the following: time of the day; location; ambient light levels; proximity sensing; historical user behavior patterns. Some or all of the metadata may be collected by the system 400 or by an ancillary device that cooperates or communicates with the system 400, as mentioned above.

User status data used to track certain aspects of a user's behavior may be stored locally inside memory 416 of the system 400 and processed locally using the controller 408 of the system 400. User status data may also be transferred to the medication delivery system 102, the patient care application 110, and/or one or more of the database 114 mentioned above with reference to FIG. 1 (such that the user status data can be processed, analyzed, or otherwise utilized by the applications or components that receive the user status data). It is also possible that some of the processing and analysis are performed locally by the system 400, while further processing and analysis are performed by one or more other components of the system 100.

The detection of the start of a behavior event, such as the start of a work activity, may trigger the power up and/or activation of additional sensors and circuitry, such as a camera 418. Power up and/or activation of additional sensors and circuitry may occur at the same time as the detection of the behavior event of interest or some time thereafter. Specific sensors and circuitry may be turned on only at specific times during a detected event and may be switched off otherwise to conserve power. It is also possible that the camera 418 only gets powered up or activated upon explicit user intervention such as, for example, pushing and holding a button 420. Releasing the button 420 may turn off the camera 418 to conserve power.

When the camera 418 is powered up, a projecting light source 422 may also be enabled to provide visual feedback to the user about the area that is within view of the camera or to otherwise illuminate the field of view. Alternatively, the projecting light source 422 may only be activated sometime after the camera 418 has been activated. In certain cases, additional conditions may need to be met before the projecting light source 422 is activated. Such conditions may include: the determination that the projecting light source 422 is likely aiming in the direction of the object of interest; the determination that the system 400 is not moving excessively; or the like. In some embodiments, one or more light emitting diodes (LEDs) 426 may be used as the projecting light source 422.

Images may be tagged with additional information or metadata such as: camera focal information; proximity information from the proximity sensor 412; ambient light levels information from an ambient light sensor 424; timestamp information; etc. Such additional information or metadata may be used during the processing and analysis of the user status data.

The projecting light source 422 may also be used to communicate other information. As an example, an ancillary device may use inputs from one or more proximity sensors 412, process those inputs to determine if the camera 418 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 422 may also be used in combination with the ambient light sensor 424 to communicate to the user if the ambient light is insufficient or too strong for an adequate quality image capture. The projecting light source 422 may also be used to communicate information including, but not limited to, a low battery situation or a functional defect.

The projecting light source 422 may also be used to communicate dietary coaching information. As an example, the projecting light source 422 might, among other things, indicate if not enough or too much time has expired since a previous food intake event, or may communicate to the user how he/she is doing against specific dietary goals.

Signaling mechanisms to convey specific messages using one or more projecting light sources 422 may include, but are not limited to, one or more of the following: specific light intensities or light intensity patterns; specific light colors or light color patterns; specific spatial or temporal light patterns. Multiple mechanisms may also be combined to signal one specific message.

A microphone 428 may be used by the user to add specific or custom labels or messages to a detected event and/or image. In certain embodiments, audio captured by the microphone 428 can be processed to assist in the determination of whether the user is eating, drinking, commuting, exercising, working, or resting. Audio snippets may be processed by a voice recognition engine.

In certain embodiments, the accelerometer 406 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the system 400 may include or cooperate with any number of other sensors 430 as appropriate for the particular embodiment. For example, and without limitation, the system 400 may include or cooperate with any or all of the following: a heartrate monitor; a physiological characteristic or analyte sensor; a continuous glucose monitor; a GPS receiver; and any other sensor, monitor, or detector mentioned elsewhere herein. The system 400 obtains user status data from one or more of its sensors, detectors, and sources, wherein the user status data indicates a stressful activity of the user. The user status data can be analyzed and processed by the system 400 (and/or by one or more other components of the system 100) to determine whether the user's current behavior is consistent with normally expected behavior or activity. In certain embodiments, the system 400 and/or an ancillary system 106 or device determines the user's activity and related behavior primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the system 400 includes at least one haptic interface 440 that is suitably configured and operated to provide haptic feedback as an output. The at least one haptic interface 440 generates output(s) that can be experienced by the sense of touch by the user, e.g., mechanical force, vibration, movement, temperature changes, or the like. Haptic feedback generated by the at least one haptic interface 440 may represent or be associated with one or more of the following, without limitation: reminders; alerts; confirmations; notifications; messages; numerical values (such as measurements); status indicators; or any other type of output provided by the system 400.

In certain embodiments, the user status data (e.g., sensor data) is provided to a gesture recognizer unit or processor. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs (such as the output from one or more ancillary systems 106) to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processor. The event detector analyzes the incoming stream of gestures to determine if the start of an event of interest (e.g., eating a meal, going to bed, working out) has occurred, whether an event is ongoing, whether an event has ended, or the like. Although this description mentions meal detection, the gesture-based physical behavior detection system 400 may be suitably configured to monitor other types of physical behavior or activities. Such activities include, without limitation: reading; sleeping; smoking; getting dressed; driving; walking; commuting; working; exercising; turning down a bed; making a bed; brushing teeth; combing hair; talking on the phone; inhaling or injecting a medication; and activities related to hand hygiene or personal hygiene.

Figure 9:
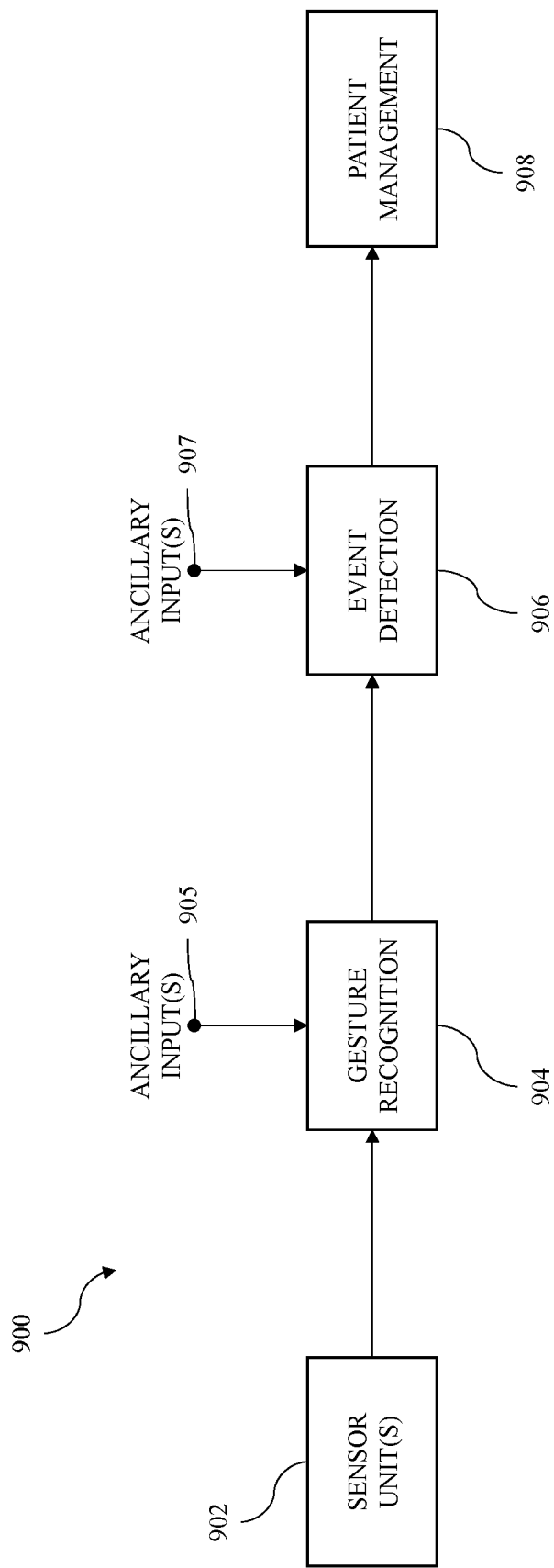
FIG. 9 is a block diagram representation of an embodiment of a gesture-informed patient management system in accordance with certain embodiments.

FIG. 9 is a simplified block diagram representation of an embodiment of a gesture-informed patient management system 900. The depicted patient management system 90 includes, without limitation, one or more sensor units 902, a gesture recognition unit 904, an event detection unit 906, and a patient management unit 908.

The sensor unit(s) 902 generally represent the sensor(s) embedded in, integrated with, or otherwise associated with one or more portable or wearable devices associated with a patient, such as, for example, an activity tracker, a smart watch, a wristband, a ring, a mobile phone, or a portable electronic medical device (e.g., a continuous glucose monitoring device, an infusion device, an injection pen, and/or the like). For example, in one or more exemplary embodiments, the sensor unit(s) 902 include an accelerometer (e.g., accelerometer 406) and a gyroscope (e.g., gyroscope 412) associated with a smart watch. That said, it should be appreciated the patient management system 900 is not limited to any particular type, configuration, or number of sensor unit(s) 902, and in practice, the sensor unit(s) 902 may include one or more of the following sensing arrangements: accelerometers, gyroscopes, magnetometers, image sensors, cameras, optical sensors, proximity sensors, pressure sensors, odor sensors, gas sensors, aspiration sensors, oximeters, Global Positioning Systems (GPS) receivers, microphones, galvanic skin response sensors, thermometers, ambient light sensors, UV sensors, electrodes for electromyographic ("EMG") potential detection, bio-impedance sensors, spectrometers, glucose sensors, heart rate sensors, pulse sensors, touchscreen or capacitive sensors. In this regard, the output of the sensor unit(s) 902 may include any sort of motion data, location data, physiological data (e.g., temperature, heart rate, pulse, galvanic skin response, blood or body chemistry, and/or the like), or other sensor data depending on the sensor type. The output of the sensor unit(s) 902 may be communicated to the gesture recognition unit 904 wirelessly or via wires, in analog or digital form, directly or indirectly (e.g., intermediated by gating and/or clocking circuits, analog-to-digital converters, and/or the like).

As described in greater detail below, in exemplary embodiments, the sensor units 902 include a primary sensor unit corresponding to a portable or wearable device associated with a patient, such as, for example, an activity tracker, a smart watch, a wristband, or the like, and one or more secondary sensor units that provide measurement data utilized to inform, refine, augment, or otherwise enhance the detection of gestures or gestured events based on the measurement output from the primary sensor unit. In this regard, the secondary sensor unit(s) may be associated with different locations on the patient's body than the location of the primary sensor unit, or the secondary sensor unit(s) may be independent of the patient's body. For example, in some embodiments, the secondary sensor unit(s) may be fixed or stationary and provide a reference for measuring the patient's movement or behavior relative to that reference. The secondary sensor units may be realized using the patient's other portable or wearable devices (e.g., a CGM device, an infusion device, a smart injection pen, a mobile phone, and/or the like) or be realized using other electronic devices that are not associated with the patient (e.g., a Bluetooth low energy (BLE) beacon, an ultra-wideband beacon, or the like). The secondary sensor units may also employ different types of sensors or sensing technologies than the primary sensor unit. For example, the primary sensor unit may utilize an accelerometer and/or gyroscope for measuring wrist or hand movements by the patient, while the secondary sensor unit may utilize proximity sensors, location sensors, pressure sensors, audio sensors, or the like.

The gesture recognition unit 904 generally represents a software application or component of the patient management system 900 that receives the sensor data signals from the sensor unit(s) 902 and analyzes the received sensor data to detect or otherwise identify gestures performed by the patient based on the received sensor data. In this regard, a gesture generally represents a discrete set of one or more physical movements having associated spatial and/or temporal characteristics that are distinguishable from other gestures. For example, as described in United States Patent Publication Number 2020/0289373, the gesture recognition unit 904 may utilize machine learning or other artificial techniques to map different subsets of sensor data within a stream of received sensor data to different gesture features, which, in turn, are then analyzed to classify or otherwise resolve the different subsets of the sensor data and corresponding gesture features into a particular combination or sequence of gestures performed by the patient. In one or more embodiments, the gesture recognition unit 904 fuses or otherwise combines concurrent or otherwise temporally-associated accelerometer data and gyroscope data to obtain an orientation vector, with the concurrent or temporally-associated combinations of accelerometer data, gyroscope data, and fused orientation vectors being input to a feature generator, which, in turn, generates a corresponding stream of gesture features, which, in turn are input to the gesture recognition model which classifies or otherwise resolves the stream of gesture features into corresponding gestures. In exemplary embodiments, the gesture recognition unit 904 also associates or otherwise assigns a confidence metric to each gesture based on the gesture features. In this regard, for a given stream of sensor data received by the gesture recognition unit 904, the gesture recognition unit 904 outputs a corresponding stream of gestures and associated confidence levels.

In some embodiments, the gesture recognition unit 904 receives one or more ancillary inputs 905 which may influence the gesture detection or the confidence or probability assigned to detected gestures. For example, the ancillary input 905 may include operational contextual data, such as, the current time of day, the current day of the week, the current month of the year, the current location of the patient, and/or the like, along with other patient-specific data such as historical gesture data associated with the patient, a patient profile associated with the patient or other patient-specific personalization that may be utilized by the gesture recognition unit 904 to influence manner in which particular gesture features are mapped to a gesture for the particular patient. In this regard, statistical analysis of the historical gesture data and potentially other patient-specific data may be utilized to determine or otherwise assign probabilities of a specific gesture occurring based on the current operational context. It should be noted that there are any number of different types of ancillary input data that may be correlative to the occurrence or non-occurrence of a particular gesture, and the subject matter described herein is not limited to any particular type or combination of ancillary inputs 905 that may be utilized by the gesture recognition unit 904.

In one or more embodiments, the executable code or programming instructions corresponding to the gesture recognition unit 904 is stored or otherwise maintained in a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by a processor or other processing system. For example, in one or more exemplary embodiments, the computer-executable programming instructions corresponding to the gesture recognition unit 904 are stored in a data storage element (e.g., memory 416) of a wearable electronic device including the sensor unit(s) 902, and, when read and executed by a processing system (e.g., controller 408) of the wearable electronic device, the instructions cause the wearable electronic device to generate the gesture recognition unit 904 at the wearable electronic device. In this regard, in some embodiments, the wearable electronic device may transmit or otherwise provide signals or data indicating a stream of detected gestures and associated confidence levels to another device for further processing and/or analysis. That said, in other embodiments, the gesture recognition unit 904 may be implemented at or on a patient's mobile phone or other portable electronic device (e.g., user device 108) that receives sensor data signals from the sensor unit(s) 902 via a wireless network, or be implemented at or on a cloud computing system or remote server that receives the sensor data signals from the sensor unit(s) 902 via the Internet, a cellular network, or the like.

Still referring to FIG. 9, the event detection unit 906 generally represents a software application or component of the patient management system 900 that receives the detected gestures and confidence levels from the from the gesture recognition unit 904 and analyzes the received gesture data to detect or otherwise identify events or activities performed by the patient based on the received gesture data. For example, as described in United States Patent Publication Number 2020/0289373, the event detection unit 906 may utilize machine learning or other artificial techniques to map a stream of detected gestures and associated confidence levels into a particular event or activity being performed by the patient based on the type of gestures detected, the sequence of detected gestures, the temporal relationship between gestures and/or the confidence metrics assigned to the detected gestures. In this manner, the event detection unit 906 may map lower-level gestures into a higher-level physical behavior while filtering or otherwise deemphasizing false positives or spurious gestures. Thus, for a given stream of detected gestures received by the event detection unit 906, the event detection unit 906 outputs an indication of a detected event or activity by the patient and an associated confidence or probability metric for the event. For example, for a sequence of detected food intake gestures may be mapped or otherwise recognized as a food intake event having a particular start time, pace, duration, and/or the like with an assigned level of confidence or probability influenced by the confidence associated with the detected food intake gestures and potentially other factors.

In a similar manner as described above for the gesture recognition unit 904, the event detection unit 906 may receive ancillary input 907 which may influence the event detection or the confidence or probability assigned to detected events. For example, the ancillary input 907 may include event log data associated with the patient that maintains data pertaining to historical events or activities by the patient (e.g., meals, exercise, sleep, boluses, glucose excursion events, and/or the like), with statistical analysis of the historical event log data and potentially other patient-specific data being utilized to determine or otherwise assign probabilities of a specific event occurring based on the current operational context. In this regard, if the patient habitually engages in meals at or around a certain time of day, food intake gestures occurring at that time of day consistent with the patient's historical behavior may be more likely to be mapped to a meal event or other food intake event, or the detected meal event or food intake event may be assigned a higher probability or confidence value based on the correlation and consistency with the patient's historical behavior. Again, it should be noted that there are any number of different types of ancillary input data that may be correlative to the occurrence or non-occurrence of a particular event, and the subject matter described herein is not limited to any particular type or combination of ancillary inputs 907 that may be utilized by the event detection unit 906.

In one or more embodiments, the executable code or programming instructions corresponding to the event detection unit 906 is stored or otherwise maintained in a data storage element or memory, including any sort of short or long term storage media or other non-transitory computer-readable medium, which is capable of storing programming instructions for execution by a processor or other processing system. For example, in one or more exemplary embodiments, the computer-executable programming instructions corresponding to the event detection unit 906 are stored in a data storage element (e.g., memory 416) of a wearable electronic device including the sensor unit(s) 902, and, when read and executed by a processing system (e.g., controller 408) of the wearable electronic device, the instructions cause the wearable electronic device to generate the event detection unit 906 at the wearable electronic device. In this regard, in some embodiments, the wearable electronic device may transmit or otherwise provide signals or data indicating a stream of detected events and associated confidence or probability levels to another device for further processing and/or analysis. That said, in other embodiments, the event detection unit 906 may be implemented at or on a patient's mobile phone or other portable electronic device (e.g., user device 108) or on a cloud computing system or remote server that receives gesture data signals from the gesture recognition unit 904 implemented at another device via a network.

Still referring to FIG. 9, the patient management unit 908 generally represents a software application or component of the patient management system 900 that receives the detected event data from the event detection unit 906 and automatically initiates or otherwise performs one or more actions with respect to management of the patient's physiological condition. In some embodiments, the patient management unit 908 is configurable to support one or more autonomous operating modes for an infusion device, a smart pen, or other fluid delivery device, where the patient management unit 908 calculates or otherwise determines dosage commands for operating an actuation arrangement to deliver fluid to the patient. For example, in a closed-loop operating mode, the patient management unit 908 may determine a dosage command based at least in part on a current glucose measurement value for the patient in a manner that is influenced by an event detected by the event detection unit 906. In some embodiments, the patient management unit 908 is configurable to generate or otherwise provide user notifications or alerts via a user interface element based at least in part on a detected event. In this regard, the patient management unit 908 may utilize patient-specific settings, preferences, or other notification criteria to automatically generate user notifications in a manner that is influenced by the detected event and potentially other factors (e.g., the patient's current or recent sensor glucose measurement values). For example, in one or more embodiments, for a patient on a MDI therapy regimen where the medication delivery system 102 includes a smart pen or other injection device, the patient management unit 908 may utilize patient-specific settings, preferences, or other notification criteria to automatically generate user notifications that indicate recommended bolus amounts, a recommended time (or window of time) for when a bolus should be delivered, and/or the like to assist the patient in administering an appropriate bolus that is responsive to a gestured event.

In one or more embodiments, the executable code or programming instructions corresponding to the patient management unit 908 is stored or otherwise maintained at one of the patient's associated devices (e.g., the patient's mobile phone, the patient's infusion device or other fluid delivery device, portable electronic device, or the like) or at a cloud computing system or remote server. For example, the patient management unit 908 executing on the patient's phone may receive or otherwise obtain signals or data indicating detected gestures and/or events from the patient's smart watch or other wearable device, analyze the received data, and transmit or otherwise provide dosage commands or signals influenced by the detected gestured-based events to the patient's infusion device (e.g., via a wireless network) to automatically operate the infusion device to deliver insulin or another fluid or medicament to account for the detected event(s), or the patient management unit 908 may generate GUI displays or other user notifications influenced by the detected event(s) at the mobile device. That said, in other embodiments, when the patient management unit 908 is implemented at a remote server or other cloud computing system, the patient management unit 908 may transmit or otherwise provide dosage commands or signals to a device associated with the patient via a network. In yet other embodiments, the patient management unit 908 may be implemented at the patient's medical device and receive detected event data from the patient's mobile device, the patient's wearable device, or a remote server or other cloud computing system. In this regard, depending on the embodiment, the various units 904, 906, 908 may be distributed across one or more different devices 102, 104, 106, 108, 116 in a system 100 and the subject matter described herein is not limited to any particular implementation. For example, the event detection unit 906 and the patient management unit 908 may be implemented by the patient care application 110 at the user device 108 receiving the detected gesture data stream signals output by the gesture detection system 104 from the gesture detection system 104 via a wireless network.

Figure 10:
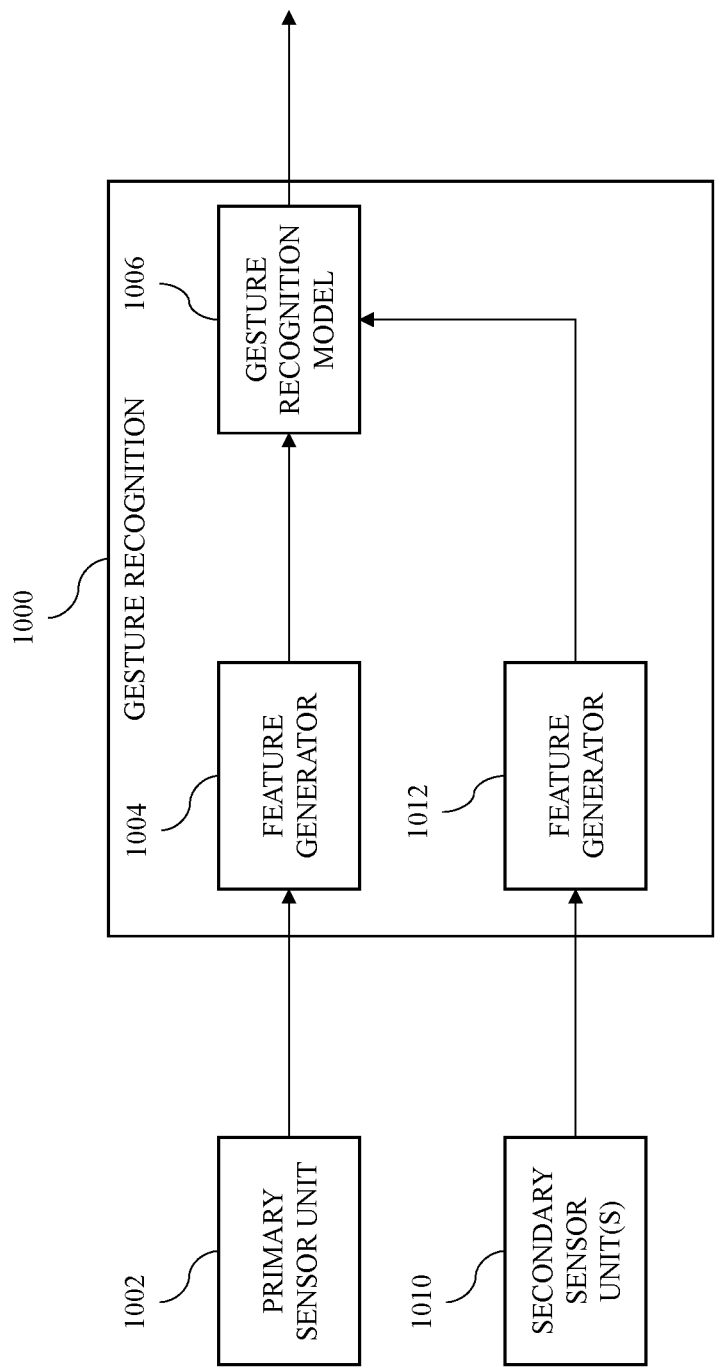
FIG. 10 is a block diagram representation of an embodiment of a gesture recognition unit suitable for use in the gesture-informed patient management system in accordance with one or more exemplary embodiments.

FIG. 10 depicts an exemplary embodiment of a gesture recognition unit 1000 suitable for use as the gesture recognition unit 904 in the patient management system 900 of FIG. 9 to augment or otherwise refine the accuracy of gestures detected based on the output of a primary sensor unit 1002 using one or more secondary sensor units 1010. In this regard, the primary sensor unit 1002 generally represents the one or more sensor(s) embedded in, integrated with, or otherwise associated with a wearable device associated with a patient for monitoring or tracking physical movements of the patient, such as, for example, a smart watch, a wrist band, an activity tracker, or the like. The secondary sensor unit(s) 1010 generally represent the one or more sensor(s) embedded in, integrated with, or otherwise associated with another device associated with the patient. For example, in some embodiments, a secondary sensor unit 1010 is realized as a smart watch, a wrist band, an activity tracker, or another wearable device associated with the patient for monitoring or tracking physical movements of the patient redundant to the primary sensor unit 1002. That said, in other embodiments, the secondary sensor unit(s) 1010 may be realized using different types of devices, which may include different sensors associated therewith or otherwise leverage different sensing technologies, and the subject matter described herein is not limited to any particular type, number, or combination of secondary sensor unit(s) 1010.

In a similar manner as described above in the context of FIG. 9, in one or more exemplary embodiments, the primary sensor unit 1002 includes an accelerometer (e.g., accelerometer 406) that outputs or otherwise provides signals or data indicative of a measured acceleration associated with the primary sensor unit 1002, and the primary sensor unit 1002 also includes a gyroscope (e.g., gyroscope 412) that outputs or otherwise provides signals or data indicative of a measured angular velocity associated with the primary sensor unit 1002. In this regard, in one or more embodiments, the primary sensor unit 1002 is configured to fuse or otherwise combine the measured acceleration and the measured orientation to obtain a fused orientation vector. The gesture recognition unit 1000 includes a feature generator 1004 that utilizes machine learning or other artificial techniques to map different subsets of sensor data within a stream of received sensor data to different gesture features. In this regard, the measured acceleration, measured angular velocity, and fused orientation data signals received by the gesture recognition unit 1000 are converted, classified, mapped or otherwise resolved to different gesture features that may be made by the patient's hand or wrist.

Likewise, the illustrated embodiment of the gesture recognition unit 1000 employs one or more additional feature generators 1012 associated with the one or more secondary sensor unit(s) 1010. The secondary sensor feature generator 1012 similarly utilizes machine learning or other artificial techniques to map different subsets of sensor data within a stream of received sensor data to different gesture features. For example, in one or more embodiments, the secondary sensor unit 1010 includes or is otherwise realized an in-ear sensor unit (e.g., in-ear headphone(s) or earbud(s)) that also includes an accelerometer that outputs or otherwise provides signals or data indicative of a measured acceleration associated with the secondary sensor unit 1010 and a gyroscope that outputs or otherwise provides signals or data indicative of a measured angular velocity associated with the secondary sensor unit 1010. In this regard, the feature generator 1012 may be trained using machine learning or other artificial techniques to map different subsets of accelerometer and/or gyroscope data within a stream of received sensor data from the secondary sensor unit 1010 to different gesture features that may be made by the patient's head. In this manner, the measured acceleration, measured angular velocity, and fused orientation data signals from the secondary sensor unit 1010 may be converted, classified, mapped or otherwise resolved to different head gesture features. For example, a particular combination of values (or a range of value combinations) for the measured acceleration, measured angular velocity, and fused orientation associated with the patient's head may be mapped to a chewing gesture feature, while another combination may be mapped to a food intake gesture feature, a drinking gesture feature, a speaking gesture feature, and/or the like. In yet other embodiments, additionally or alternatively to an accelerometer and a gyroscope, an in-ear secondary sensor unit 1010 could include a pressure sensor, a microphone, a proximity sensor, a location sensor, or any other suitable type of sensor or combination thereof that provides sensed output data signals capable of being mapped to a particular head gesture feature by the feature generator 1012.

In one or more embodiments, the secondary sensor unit 1010 is realized as one or more sensors of a CGM device that is attached or otherwise worn on a patient's upper arm or other part of the patient's body. In this regard, similar to the primary sensor unit 1002, the secondary sensor unit 1010 of the CGM device may include an accelerometer and/or a gyroscope and output measured acceleration, measured angular velocity, and fused orientation data signals that may be converted, classified, mapped or otherwise resolved to different arm gesture features by the feature generator 1012. For example, the feature generator 1012 may map a particular combination of values (or a range of value combinations) for the measured acceleration, measured angular velocity, and fused orientation associated with the patient's upper arm to a food intake gesture feature, while another combination may be mapped to a drinking gesture feature, and/or the like.

In the illustrated embodiment of FIG. 10, the features output by the feature generators 1004, 1012 are provided as input variables to a gesture recognition model 1006, which is trained using machine learning or other artificial techniques to map different combinations and/or sequences of gesture features derived from the outputs of the different sensor units 1002, 1010 into a particular combination or sequence of gestures performed by the patient. In exemplary embodiments, the gesture recognition model 1006 also associates or otherwise assigns a confidence metric to each gesture based on the gesture features. In this regard, based on the relationship between the primary sensor gesture features and the secondary sensor gesture features, the gesture recognition model 1006 may more accurately recognize and assign higher confidence levels to gestures when the primary sensor gesture features and the secondary sensor gesture features are physically and/or temporally consistent with one another. For example, when food intake gesture feature output by the primary sensor feature generator 1004 precedes a chewing gesture feature or other food intake feature output by the secondary sensor generator 1012 (e.g., based on the output of an in-ear secondary sensor unit 1010) within a threshold period of time after the primary sensor food intake gesture feature, the gesture recognition model 1006 may recognize a food intake gesture and assign a higher confidence level based on the in-ear gesture feature confirming the primary sensor food intake gesture feature by being physically and temporally consistent with the patient consuming food. On the other hand, the gesture recognition model 1006 exhibit fewer false positives or otherwise assign lower confidence levels to gestures when the primary sensor gesture features and the secondary sensor gesture features are physically and/or temporally inconsistent with one another. For example, when food intake gesture feature output by the primary sensor feature generator 1004 is not followed by a chewing gesture feature or other food intake feature output by the secondary sensor generator 1012 (e.g., based on the output of an in-ear secondary sensor unit 1010) within a threshold period of time after the primary sensor food intake gesture feature, the gesture recognition model 1006 may fail to recognize a food intake gesture or assign a lower confidence level to the food intake gesture in the absence of the in-ear gesture feature confirming the primary sensor food intake gesture feature.

By utilizing the output of one or more additional secondary sensor units 1010 in addition to the primary sensor unit 1002, the gesture recognition model 1006 can be trained using the inputs from different sensors at different physical devices and locations to create a model that better reconstructs the patient's movements by relating the hand or wrist gestures derived from a wrist-work primary sensor unit 1002 with relative to other parts of the body. For example, when the secondary sensor unit 1010 is realized using a CGM device worn on the patient's upper arm, the combination of sensor data from motion sensors located on the wrist or hand with sensor data from motion sensors located on the upper arm allows the gesture recognition model 1006 to reconstruct and estimate the position, movement and rotation of the upper arm with respect to the lower arm, and vice versa, thereby allowing for a more accurate estimation or prediction of what gestures the patient is performing with his or her arm and increase the confidence level accordingly. In this regard, when the primary sensor measurement data and the secondary sensor measurement data are positively correlated with one another and correspond to the same gesture being performed by the patient, the gesture recognition model 1006 may detect that gesture based on the correlation between the primary sensor measurement data and the secondary sensor measurement data and/or assign a higher confidence value to the detected gesture based on the correlation between the primary sensor measurement data and the secondary sensor measurement data.

For example, based on sensor data received from motion sensors (e.g., an accelerometer and/or gyroscope) embedded in a wrist-worn wearable, the gesture recognition model 1006 may detect certain gesture feature(s) by a user is likely a food intake gesture and assign an initial probability or confidence level that the wrist-based gesture feature(s) have been correctly detected and classified. By taking into account gesture feature inputs from one or motion sensors embedded in a device worn on the upper arm (e.g., an accelerometer and/or gyroscope embedded in a CGM device), the gesture recognition model 1006 may determine that the upper arm movement was too much or too fast for a typical food intake gesture by the patient, or too little or too slow for a typical food intake gesture by the patient. As a result, the gesture recognition model 1006 may not classify the gesture feature(s) from the wrist-worn sensors as a food intake gesture or reduce the probability or confidence level that the wrist-based gesture feature(s) have been correctly detected and classified. In this regard, the gesture recognition model 1006 may be trained or otherwise configured to analyze and identify combinations of wrist-based (or lower arm-based) gesture features and upper-arm gesture features that are likely to be a food intake gesture, for example, because the combination of inputs indicates that the hand is near the mouth when it comes to a standstill or near-standstill, and that the hand and arm movement corresponds to a typical plate to mouth trajectory.

Still referring to FIG. 10 with reference to FIG. 9, in one or more embodiments, the event detection unit 906 may be trained or otherwise configured similar to the gesture recognition unit 1000 to augment or otherwise refine the accuracy of events detected based on the output of the gesture recognition unit 904, 1000 using one or more secondary sensor units 1010. For example, the detected gesture data stream output by the gesture recognition unit 904, 1000 (e.g., indicia of detected gestures, confidence levels, and potentially other attributes associated therewith) may be provided as input variables to an event detection model that also receives as input variables secondary sensor features output by a corresponding feature generator (e.g., feature generator 1012). In this regard, the event detection model employed by the event detection unit 906 may be trained using machine learning or other artificial techniques to map different combinations and/or sequences of detected gestures output by the gesture recognition unit 904, 1000 and secondary sensor gesture features derived from the output(s) of the secondary sensor unit(s) 1010 into the occurrence of a particular type of event with an assigned confidence metric associated therewith. Thus, based on the relationship between the detected primary sensor gestures and the secondary sensor gesture features, the event detection model may more accurately recognize and assign higher confidence levels to events when the secondary sensor gesture features are physically and/or temporally consistent with a gestured event corresponding to the primary sensor gestures. In this regard, when the gesture(s) detected based on the primary sensor measurement data and the secondary sensor measurement data are positively correlated with one another and both correspond to occurrence of the same event, the event detection model may more accurately predict occurrence of that event based on the correlation between the detected gesture(s) and the secondary sensor measurement data and/or assign a higher confidence value to the predicted event occurrence based on the correlation between the detected gesture(s) and the secondary sensor measurement data.

In some embodiments, the event detection unit 906 may detect or otherwise recognize a physical behavior event or other gestured event using secondary sensor input data that is independent of the patient's hand movements, positions or gestures. For example, the output of an in-ear sensor unit or other head-worn sensor unit may be analyzed by the event detection unit 906 to detect or otherwise confirm a food intake event indicated by the primary sensor gesture data and/or assign attributes or characteristics to the food intake event based on sensor measurement data and corresponding secondary sensor gestures indicative of swallowing patterns, mouth and lip movements, movement of cheeks or jaws, saliva, and/or the like. In some embodiments, a microphone or other audio sensor may be utilized to identify sounds from the mouth, throat or digestive system indicative of a food intake event. In other embodiments, the wrist-worn sensor gesture data may be utilized to confirm or otherwise enhance detection of an event based on other sensor measurement data. For example, if movement of a patient's cheeks or jaws indicates an actual or probable occurrence of a food intake event, monitoring hand or arm movement can provide additional insight into whether or not a food intake event has actually occurred. Monitoring hand or arm movement may also be utilized to determine one or more characteristics of a food intake event, such as the pace of eating or amount of food consumed (e.g. bite count). Thus, inputs from multiple sensors at different locations can aid in or enhance the performance of the physical behavior event detection.

It should be appreciated there are numerous different types or combinations of different sensor units that may be employed to augment or otherwise enhance gesture recognition or event detection, and the subject matter described herein is not limited to any particular primary and secondary sensor configuration. For example, in some embodiments, sensor measurements of movement of a patient's cheeks or jaws may then be used to increase the confidence level or provide additional insight into whether or not the patient is indeed eating. As another example, measurements of a patient's heart rate, pulse, breathing pace and/or breathing patterns (e.g., via one or more motion sensors placed on a patient's chest, abdominal area, or back, a microphone or audio sensor, and/or the like), and/or the like may be utilized in concert with wrist-worn sensor data to detect occurrence of an exercise event, a sleep event, a smoking event and/or the like. It should also be noted that although the subject may be described herein in the context of sensors embedded in wearable devices, in various embodiments, secondary sensors could be embedded in clothing or in the body of the patient (e.g., via a tattoo or implant), or in a device that is attached or inserted in the patient's body (e.g., a CGM device, an infusion device, a smart injection pen, and/or the like).

In one or more embodiments, a sensor on the wrist may be utilized to monitor electrical muscle activation signals, which, in turn, may be analyzed to derive feature gestures corresponding to the pose of a patient's wrist, hand and/or fingers. For example, the secondary sensor unit may be realized as a sensor that senses muscle activation for obtaining corresponding muscle activation gesture features that may be utilized to more accurately classify and better differentiate wrist-worn motion sensor gesture features.

In various embodiments, the secondary sensor unit 1010 is realized as an in-ear device that includes one or more motion sensors, pressure sensors, vibration sensors, electrical muscle activation sensors, audio sensors, bone conduction sensors, and/or the like. In the case of an in-ear secondary sensor unit 1010, the feature generator 1012 may be trained to develop a model that detects the specific characteristics and signatures of the in-ear sensor unit 1010 output which are indicative of eating, speaking, drinking, swallowing, chewing, smoking, yawning, coughing, sneezing, spitting, burping, snoring, sipping, and/or the like. As described above, the output of the in-ear sensor feature generator 1012 may be provided to the gesture recognition model 1006 that is trained to utilize the in-ear sensor gesture features to derive further insights and enhance or otherwise augment gesture detection based on primary sensor feature gestures to increase confidence associated with detected gestures and mitigate false positives. In an equivalent manner, the output of the in-ear sensor feature generator 1012 may be provided to an event detection model that is trained to utilize the in-ear sensor gesture features to derive further insights and enhance or otherwise augment event detection based on detected patient gestures using the primary sensor to increase confidence associated with the detection or prediction of gestured events.

In-ear sensor output may also be utilized to assign different attributes to detected gestures and/or events, for example, by identifying different signal characteristics or signatures capable of differentiating different food types (e.g., crunchy, soft, chewy, tender, liquid, etc.). More accurately detecting and assigning attributes or characteristics to a food intake event input to the patient management unit 908 may improve insulin dosing recommendations or other insulin delivery commands or adjustment generated by the patient management unit 908 to improve glycemic control. For example, if the patient's historical meal data indicates the patient usually eats one of a select few different breakfast meals, the in-ear secondary sensor output may be utilized to identify the particular one of the breakfast meals currently being consumed (e.g., cereal if the detected food type is crunchy or an omelet if the detected food type is soft), thereby allowing the patient management unit 908 to determine the patient's estimated or expected insulin requirements based on the patient's historical data associated with that respective type of breakfast. In this regard, the patient management unit 908 may automatically generate a bolus dosage command or recommendation based on the patient's historical meal and glucose data for prior instances of the detected food type or otherwise automatically adjust operation of a fluid delivery device in anticipation of a particular glycemic response for the patient based on the patient's historical data. For example, if the patient typically requires 20 units of insulin for a crunchy breakfast, the patient management unit 908 may automatically generate a bolus dosage command for 20 units of insulin or recommend a meal bolus of 20 units of insulin when the in-ear sensor unit confirms a gestured food intake event detected based on primary sensor measurement data and indicates a crunchy food type associated with the food intake event.

Still referring to FIG. 10, in some embodiments, the secondary sensor unit 1010 is duplicative or redundant of the primary sensor unit 1002, for example, to accommodate ambidextrous individuals, patient-specific idiosyncrasies (e.g., the patient uses the non-dominant hand for some activities), or other patient-specific preferences for wearable devices (e.g., a patient prefers to wear a smart watch on the non-dominant hand). For example, the primary sensor unit 1002 could be realized as a smart watch having a touch screen or other display device and related functionality, while the secondary sensor unit 1010 is realized using a lower cost, lower power wrist-worn device, such as a bracelet, band, or similar device that lacks a display device or other user interface.

In one or more embodiments, the acceleration, angular velocity, and fused orientation measurement data from the different sensor units 1002, 1010 can be provided to separate instances of feature generators and gesture recognition models before merging the outputs (e.g., using a logical or operation, a logical and operation, and/or the like). For example, if a food intake gesture is detected based on the sensor measurement data from either wrist-worn sensor unit 1002, 1010, then a food intake gesture or food intake event may be detected overall (e.g., even though the output of the primary sensor unit 1002 may not indicate food intake).

In other embodiments, the acceleration, angular velocity, and fused orientation measurement data from the different sensor units 1002, 1010 can be provided to separate instances of feature generators and fed into a gesture recognition model that detects gestures based on correlations between the sensor units 1002, 1010. For example, if the output of one sensor unit indicates a cutting motion and the output of another sensor unit indicates a fork eating motion, a food intake gesture may be detected with greater confidence.

Figure 11:
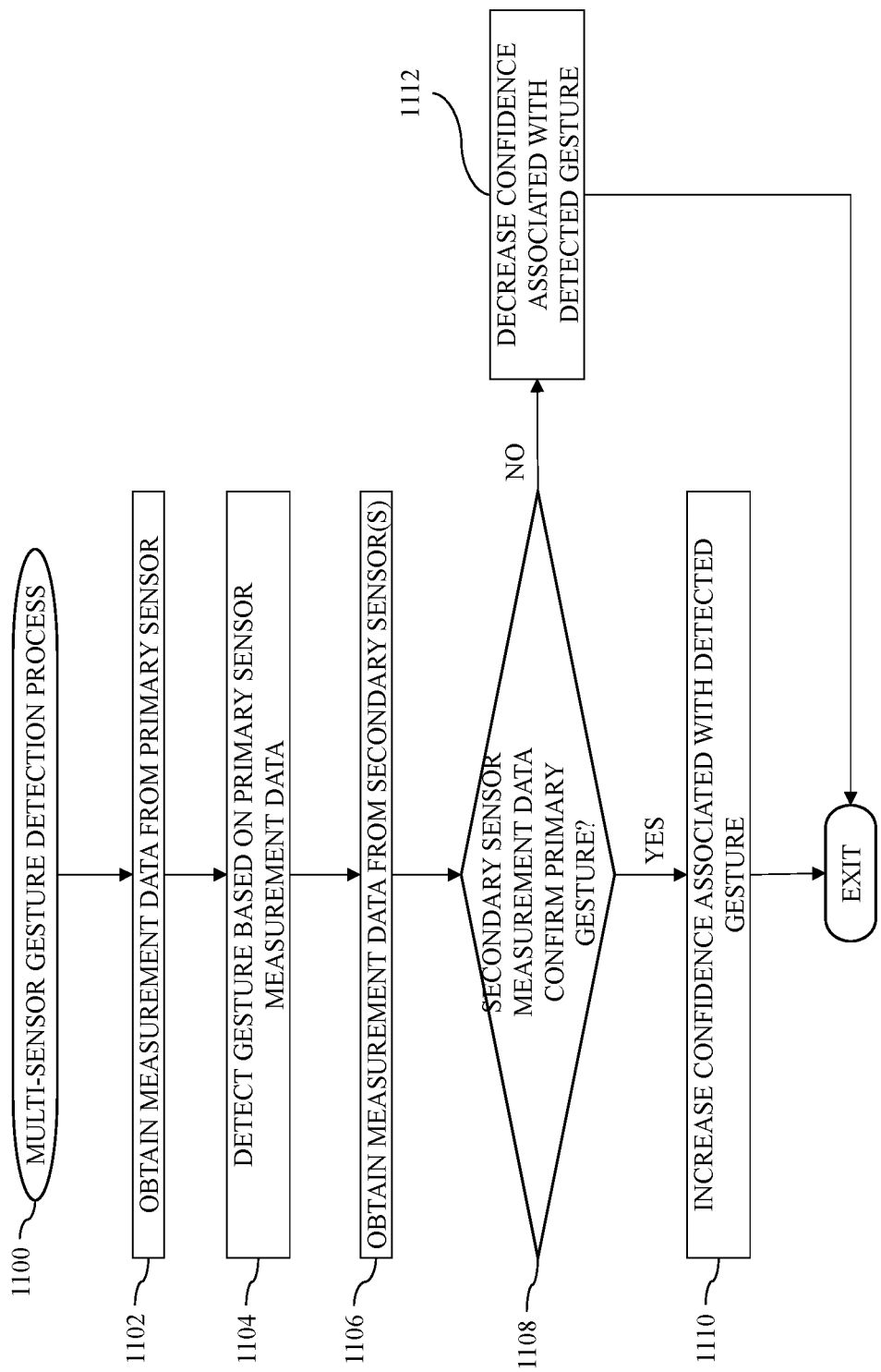
FIG. 11 is a flow diagram of an exemplary multi-sensor gesture detection process in accordance with one or more exemplary embodiments.

FIG. 11 depicts an exemplary multi-sensor gesture detection process 1100 suitable for implementation by a patient management system (e.g., patient management system 900) to augment, enhance, refine, or otherwise improve the accuracy and reliability of gestures detected based on an individual's physical movements measured by a wearable device using one or more secondary sensing devices. The various tasks performed in connection with the multi-sensor gesture detection process 1100 may be performed by hardware, firmware, software executed by processing circuitry, or any combination thereof. For illustrative purposes, the following description refers to elements mentioned above in connection with FIGS. 1-10. It should be appreciated that the multi-sensor gesture detection process 1100 may include any number of additional or alternative tasks, the tasks need not be performed in the illustrated order and/or the tasks may be performed concurrently, and/or the multi-sensor gesture detection process 1100 may be incorporated into a more comprehensive procedure or process having additional functionality not described in detail herein. Moreover, one or more of the tasks shown and described in the context of FIG. 11 could be omitted from a practical embodiment of the multi-sensor gesture detection process 1100 as long as the intended overall functionality remains intact.

The multi-sensor gesture detection process 1100 initializes or otherwise begins by receiving or otherwise obtaining measurement data indicative of a physical movement by a patient from a primary sensor arrangement and detecting or otherwise identifying a gesture performed by the patient based on the primary sensor measurement data (tasks 1102, 1104). For example, as described above in the context of FIGS. 9-10, acceleration measurement data, angular velocity measurement data, and/or orientation measurement data output by a primary sensor unit 902, 1002 may be input to a gesture recognition unit 904, 1000 that employs one or more machine learning models to detect or otherwise identify discrete physical gestures performed by the patient based on the primary sensor measurement data. In this regard, certain sequences and/or combinations of acceleration, angular velocity, and orientation measurement values may be classified or otherwise characterized as a food intake event, while other sequences and/or combinations of acceleration, angular velocity, and orientation measurement values may be classified or otherwise characterized as an exercise event, and so on.

Still referring to FIG. 11, the multi-sensor gesture detection process 1100 continues by receiving or otherwise obtaining measurement data from one or more secondary sensor arrangements and analyzing the secondary sensor measurement data to determine whether the secondary sensor measurement verifies or otherwise confirms a detected gesture identified based on the primary sensor measurement data (tasks 1106, 1108). For example, as described above in the context of FIG. 10, when the measurement data output from a secondary sensor unit 1010 corroborates or correlates with the primary sensor measurement data and/or the detected gesture based thereon, the gesture recognition unit 904, 1000 and/or gesture recognition model 1006 may determine that the secondary sensor measurement data confirms the gesture detected based on the primary sensor measurement data. In some examples, tasks 1102 and 1106 are performed concurrently and task 1108 compares measurement data from the primary sensor arrangement and one or more secondary sensor arrangements obtained from the substantially the same time period.

When the secondary sensor measurement data confirms the gesture detected based on the primary sensor measurement data, the multi-sensor gesture detection process 1100 increases the confidence metric or probability of occurrence associated with the detected gesture (task 1110). For example, if in-ear sensor (e.g., in-ear headphone(s) or earbud(s) with or without a microphone) measurement data corroborates, correlates with, or otherwise corresponds to the patient eating and the primary sensor measurement data indicates a food intake gesture, the gesture recognition unit 904, 1000 and/or the gesture recognition model 1006 may increase the confidence associated with the detected food intake gesture (e.g., from 50% to 75%). In some embodiments, increasing the confidence associated with a detected gesture correspondingly increases the confidence associated with an event detected based on that gesture. On the other hand, when the secondary sensor measurement data contradicts or otherwise fails to correspond to the gesture detected based on the primary sensor measurement data, the multi-sensor gesture detection process 1100 decreases the confidence metric or probability of occurrence associated with the detected gesture (task 1112), and thus reduce false positives. For example, if in-ear sensor measurement data contradicts or contraindicates the patient eating when the primary sensor measurement data indicates a food intake gesture, the gesture recognition unit 904, 1000 and/or the gesture recognition model 1006 may decrease the confidence associated with the detected food intake gesture (e.g., from 50% to 25%). In this regard, decreasing the confidence associated with a detected gesture correspondingly decrease the likelihood of an event being detected based on that gesture or decrease the confidence associated with a detected event in a corresponding manner. It should be noted that in some embodiments, when the secondary sensor measurement data neither confirms nor contradicts the gesture detected based on the primary sensor measurement data, the confidence associated with the detected gesture may be maintained unchanged (e.g., 50%). Thus, detected gestures confirmed by secondary sensor measurement data may be assigned a higher confidence, while detected gestures lacking confirmation by secondary sensor measurement data may be assigned an intermediate level of confidence, while detected gestures contradicted or contraindicated by secondary sensor measurement data may be assigned a lower level of confidence.

In some embodiments, the multi-sensor gesture detection process 1100 is implemented in the context of the secondary sensor measurement data being realized as location measurement data or other spatial measurement data derived from a proximity sensor, location sensor, or other location sensing technology (e.g., Bluetooth low energy (BLE) proximity sensing, ultra-wideband (UWB) real-time location sensing (RTLS)). For example, patient's CGM device, infusion device, smart injection pen, smart phone, or other electronic devices may function as a secondary sensor unit 1010 and utilize BLE proximity sensing, UWB RTLS, or other sensing technology to provide location measurement data or other spatial measurement data indicative of the pose or spatial relationship of the patient's respective devices relative to a patient's smart watch or other wrist-worn device functioning as the primary sensor unit 1002. The sensed location measurement data or other sensed spatial measurement data may be input or otherwise provided as secondary sensor measurement data to the gesture recognition unit 904, 1000 for verifying, confirming, or otherwise augmenting gestured detected based on the wrist-worn primary sensor unit 1002. For example, the spatial relationship between the patient's wrist and the patient's CGM device, infusion device, smart injection pen, or other medical device worn by the patient or attached to the patient's body may be utilized to track or otherwise monitor the movement and trajectory of the patient's wrist, and thereby allow the gesture recognition unit 904, 1000 and/or gesture recognition model 1006 to verify or otherwise confirm a food intake gesture when the movement or trajectory of the patient's wrist relative to the patient's medical device corroborates or otherwise correlates with the patient's hand traveling to the patient's mouth and increase the confidence associated with a detected food intake gesture accordingly. Conversely, when the spatial measurement data is inconsistent with or otherwise contraindicates the patient's hand traveling to the patient's mouth, the gesture recognition unit 904, 1000 and/or gesture recognition model 1006 may decrease the confidence associated with a detected food intake gesture or suppress detection of a food intake gesture based on the primary sensor measurement data. In this regard, it should be appreciated that spatial measurement data may be combined with potentially other types of secondary sensor measurement data, such as in-ear measurement data, upper arm motion data, and/or the like, to further augment and improve the confidence associated with detected gestures.

Figure 12:
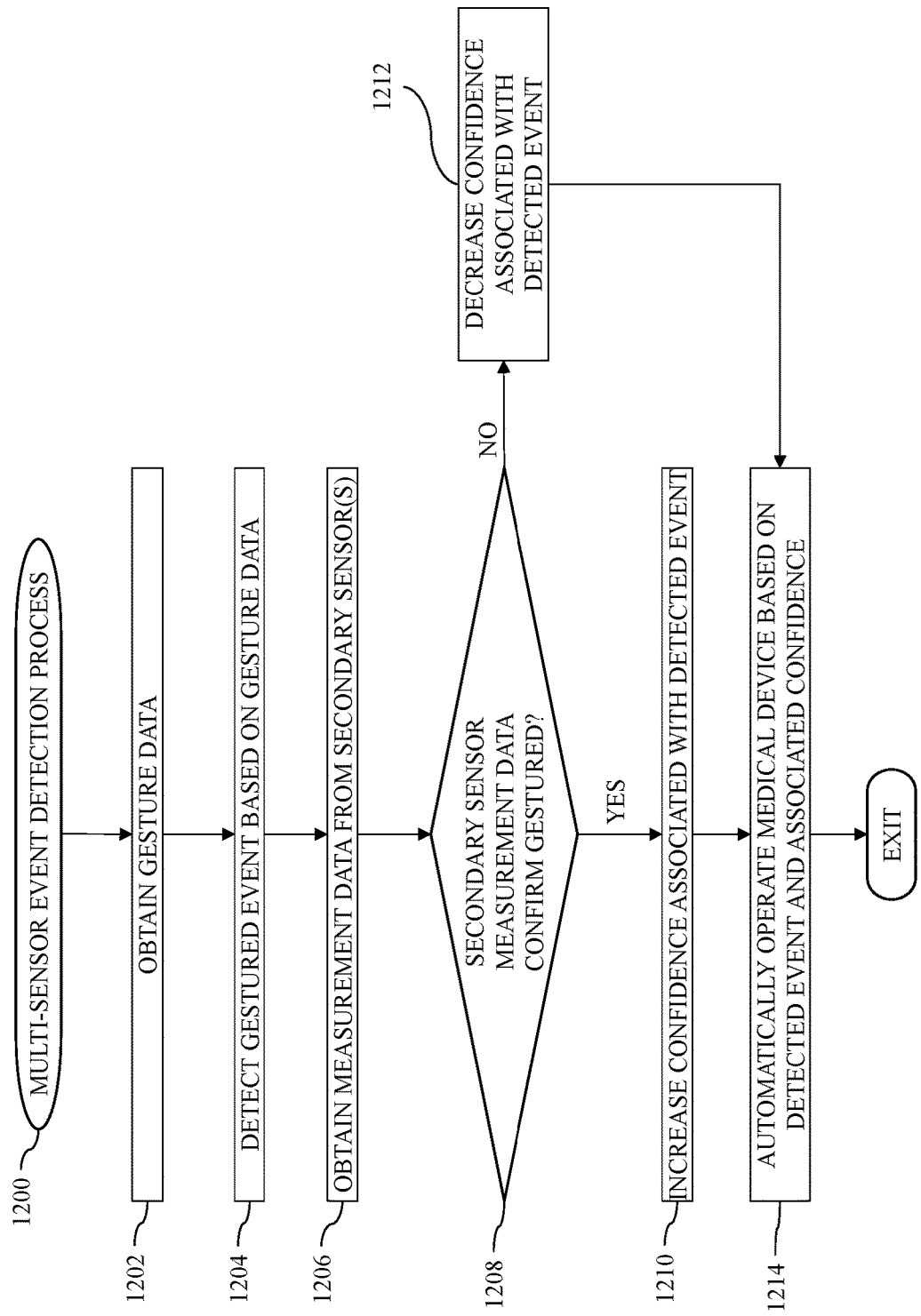
FIG. 12 is a flow diagram of an exemplary multi-sensor event detection process in accordance with one or more exemplary embodiments.

FIG. 12 depicts an exemplary multi-sensor event detection process 1200 suitable for implementation by a patient management system (e.g., patient management system 900) to augment, enhance, refine, or otherwise improve the accuracy and reliability of events detected based on an individual's physical movements measured by a wearable device using one or more secondary sensing devices. The various tasks performed in connection with the multi-sensor event detection process 1200 may be performed by hardware, firmware, software executed by processing circuitry, or any combination thereof. For illustrative purposes, the following description refers to elements mentioned above in connection with FIGS. 1-10. It should be appreciated that the multi-sensor event detection process 1200 may include any number of additional or alternative tasks, the tasks need not be performed in the illustrated order and/or the tasks may be performed concurrently, and/or the multi-sensor event detection process 1200 may be incorporated into a more comprehensive procedure or process having additional functionality not described in detail herein. Moreover, one or more of the tasks shown and described in the context of FIG. 12 could be omitted from a practical embodiment of the multi-sensor event detection process 1200 as long as the intended overall functionality remains intact.

The multi-sensor event detection process 1200 initializes or otherwise begins by receiving or otherwise obtaining gesture data indicative of gestures detected based on physical movement by a patient and detecting or otherwise identifying the probable occurrence of an event likely to influence the patient's physiological condition based on the detected gestures (tasks 1202, 1204). For example, as described above in the context of FIG. 9, the detected gesture data stream output by the gesture recognition unit 904, 1000 is received by the event detection unit 906 and analyzed (potentially in concert with one or more auxiliary inputs 907) to detect the probable occurrence of a particular type of event using a machine learning model. In this regard, the detected event may be influenced by the type of gestures detected, the number, sequence, frequency and/or timing associated with the detected gestures, the confidence associated with the detected gestures, and/or other attributes or characteristics associated with the detected gestures.

The illustrated multi-sensor event detection process 1200 continues by receiving or otherwise obtaining measurement data from one or more secondary sensor arrangements and analyzing the secondary sensor measurement data to determine whether the secondary sensor measurement verifies or otherwise confirms the gestured event (tasks 1206, 1208). In some examples, tasks 1202 and 1206 are performed concurrently and task 1208 compares measurement data from the primary sensor arrangement and one or more secondary sensor arrangements obtained from the substantially the same time period.

When the secondary sensor measurement data confirms the detected event, the multi-sensor event detection process 1200 increases the confidence metric or probability of occurrence associated with the detected event (task 1210). For example, as described above, when in-ear sensor measurement data corroborates, correlates with or otherwise corresponds to the patient eating and the detected gestures indicate a meal event or other food intake event, the event detection unit 906 may increase the confidence associated with the detected food intake event. On the other hand, when the secondary sensor measurement data contradicts or otherwise fails to correspond to the event detected based on the primary sensor gesture data, the multi-sensor event detection process 1200 decreases the confidence metric or probability of occurrence associated with the detected event (task 1212). For example, if in-ear sensor measurement data contradicts or contraindicates the patient eating when the detected gesture data stream includes a sequence of food intake gestures, the event detection unit 906 may decrease the confidence associated with the detected food intake event or otherwise suppress or fail to detect a food intake event even though the detected gesture data stream indicates a number of food intake gestures. For example, when secondary spatial measurement data is inconsistent with or otherwise contraindicates the patient's hand traveling to the patient's mouth while the detected gesture data stream indicates the patient is performing food intake gestures, the event detection unit 906 may decrease the confidence associated with a detected food intake event or suppress detection of a food intake event.

Still referring to FIG. 12, the multi-sensor event detection process 1200 continues by automatically operating a medical device based on the detected gestured event and its associated confidence (task 1214). As described above in the context of FIG. 9, the event detection unit 906 provides indicia of the detected event(s) predicted to have occurred based on the patient's gestures and the confidence or probability associated therewith to the patient management unit 908 for dynamically and automatically adjusting operation of a medical device to account for the predicted occurrence of an event. For example, based on a received meal event probability, the patient management unit 908 may automatically adjust a delivery control parameter or otherwise determine commands for adjusting delivery of insulin by an infusion device to account for the meal event (e.g., by adjusting a target glucose setpoint, an insulin delivery limit, a maximum basal insulin delivery rate, a bolus target, and/or the like). In this regard, in response to an increased probability of occurrence of a meal event, the patient management unit 908 may automatically command or otherwise adjust an infusion device or other fluid delivery device associated with the patient to increase insulin delivery or otherwise respond more aggressively to increases in the patient's sensed glucose measurement values. Conversely, when the probability or confidence associated with the predicted occurrence of a meal event is lower, the patient management unit 908 may automatically command or otherwise adjust an infusion device or other fluid delivery device to respond less aggressively.

For example, for a food intake event predicted with a confidence of 50%, the patient management unit 908 may automatically decrease the patient's target glucose setpoint value by a product of the confidence level and a maximum amount of setpoint adjustment (e.g., one half the maximum amount of setpoint adjustment), while for a food intake event with a confidence of 80%, the patient management unit 908 may automatically decrease the target glucose setpoint value by 80% of the maximum amount of setpoint adjustment, thereby allowing a glucose control system (e.g., closed loop glucose control system 300) to more aggressively respond to an increase in the patient's sensor glucose measurement values when confidence in the food intake event is higher. Thus, depending on whether or not the secondary sensor measurement data confirms or contraindicates a predicted event, the patient management unit 908 may automatically respond more or less aggressively in a manner corresponding to the increased or decreased amount of confidence derived from the secondary sensor measurement data.

As described above, in addition to adjusting the confidence or probability associated with the predicted occurrence of an event, the event detection unit 906 may adjust or otherwise determine one or more attributes associated with the predicted occurrence of an event using the secondary sensor measurement data, which, in turn, may be utilized by the patient management unit 908 in concert with the assigned confidence level to respond to the event in accordance with the secondary sensor measurement data. For example, when secondary sensor measurement data output by an in-ear sensor unit indicates a particular type of food that is likely to include a greater amount of carbohydrates or otherwise require more insulin, the event detection unit 906 may provide corresponding indicia of those predicted attributes associated with the predicted occurrence of a meal event, which, in turn, may be utilized by the patient management unit 908 to automatically adjust or configure operation of the patient's infusion device or other fluid delivery device to respond more aggressively than the patient management unit 908 may otherwise respond in the absence of the secondary sensor measurement data.

It should be noted that depending on the embodiment, the multi-sensor event detection process 1200 and the multi-sensor gesture detection process 1100 may be implemented independently or concurrently in concert with one another. In this regard, in some embodiments, different types of secondary sensor measurement data may be utilized by the multi-sensor gesture detection process 1100 to improve gesture detection, while other types of secondary sensor measurement data may be utilized by the multi-sensor event detection process 1200 to improve event detection. For example, motion measurement data from a patient's glucose sensor or CGM device affixed to the patient's arm may be utilized by the multi-sensor gesture detection process 1100 to improve gesture detection based on correlations between the patient's upper arm movement and wrist movement, while in-ear (e.g., in-ear headphone(s) or earbud(s)) measurement data may be utilized by the multi-sensor event detection process 1200 to improve event detection. Additionally, as described above, any number of different types or combinations of secondary sensor measurement data may be employed by either of the multi-sensor event detection process 1200 and the multi-sensor gesture detection process 1100 to improve confidence and accuracy.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating a medical device capable of influencing a physiological condition of a patient, the method comprising:
obtaining, by a control system associated with the medical device, first sensor measurement data from a first sensing arrangement capable of detecting physical movement by the patient, wherein the first sensing arrangement is associated with a first location on a body of the patient;
detecting, by the control system, a gesture of the patient based on the first sensor measurement data;
assigning a confidence value to the detected gesture based on the first sensor measurement data;
obtaining, by the control system, second sensor measurement data from a second sensing arrangement having a second location different from the first location, wherein both the first sensor measurement data and the second sensor measurement data correspond to the detected gesture;
adjusting by increasing or decreasing, by the control system, the confidence value of the detected gesture based on (i) a temporal relationship between first sensor measurement data and the second measurement data corresponding to the detected gesture, and (ii) corroboration or contraindication between the detected gesture and the second sensor measurement data;

predicting, by the control system, an occurrence of an event based at least in part on the detected gesture and the adjusted confidence value of the detected gesture, resulting in a predicted occurrence of the event; and configuring the medical device to influence the physiological condition of the patient in a manner that is influenced by the predicted occurrence of the event such that the medical device is configured to increase delivery of a fluid in response to the confidence value of the detected gesture being increased and in response to the corroboration between the detected gesture and the second sensor measurement data, and decrease the delivery of the fluid in response to the confidence value of the detected gesture being decreased and in response to the contraindication between the detected gesture and the second sensor measurement data.

2. The method of claim 1, wherein the adjusted confidence value is based at least in part on a correlation between the second sensor measurement data and the event.

3. The method of claim 1, wherein predicting the occurrence of the event comprises:

inputting the detected gesture and the second sensor measurement data to an event prediction model configured to output indicia of the predicted occurrence of the event.

4. The method of claim 1, wherein obtaining the second sensor measurement data comprises receiving the second sensor measurement data from an in-ear device via a wireless network.

5. The method of claim 1, wherein obtaining the second sensor measurement data comprises obtaining the second sensor measurement data from a motion sensor embedded in the medical device.

6. The method of claim 1, wherein obtaining the second sensor measurement data comprises obtaining spatial measurement data from at least one of a proximity sensor and a location sensor.

7. The method of claim 6, wherein the adjusted confidence value is based at least in part on a correlation between the first sensor measurement data and the spatial measurement data.

8. The method of claim 6, wherein the adjusted confidence value is based at least in part on a correlation between the spatial measurement data and the event.

9. The method of claim 1, wherein:

the temporal relationship comprises a temporal consistency between the first sensor measurement data and the second sensor measurement data;

the adjusting the confidence value comprises increasing the confidence value based on the temporal consistency within a threshold period of time; and the adjusting the confidence value comprises decreasing the confidence value based on the temporal consistency within the threshold period of time.

10. The method of claim 1, wherein the second measurement data is derived at least in part from electrical muscle activation signals at the second location, at least a portion of the electrical muscle activation signals corresponding to the physical movement by the patient.

11. The method of claim 1, wherein an amount of the increased delivery of the fluid is proportional to the increased confidence value, and an amount of the decreased delivery of the fluid is proportional to the decreased confidence value.

12. The method of claim 1, further comprising configuring the medical device to maintain the confidence value of the detected gesture based at least on a lack of the corroboration and a lack of the contraindication.

13. At least one non-transitory computer readable medium having stored thereon program code instructions that cause at least one processor to perform a method comprising:

obtaining first sensor measurement data from a primary sensing arrangement capable of detecting physical movement by a patient;

detecting a gesture of the patient based at least in part on the first sensor measurement data;

assigning a confidence value to the detected gesture based on one or more first gesture features corresponding to at least a portion of the first sensor measurement data;

obtaining second sensor measurement data from a secondary sensing arrangement having a different location on the patient than the primary sensing arrangement, the second sensor measurement data obtained concurrently with the first sensor measurement data;

adjusting by increasing or decreasing the confidence value of the detected gesture based at least on a temporal relationship between the one or more first gesture features and one or more second gesture features corresponding to at least a portion of the second sensor measurement data, and further based on corroboration or contraindication between the detected gesture and the second sensor measurement data;

predicting an occurrence of an event based at least in part on the detected gesture and the adjusted confidence value, resulting in a predicted occurrence of the event; and automatically configuring operation of a medical device to influence a physiological condition of the patient in a manner that is influenced by the predicted occurrence of the event by adjusting delivery of a fluid influencing the physiological condition using the medical device, the medical device configured to increase the delivery of the fluid based on the increase in the confidence value of the detected gesture based on the corroboration between the detected gesture and the second sensor measurement data, and decrease the delivery of the fluid based on the decrease in the confidence value of the detected gesture based on the contraindication between the detected gesture and the second sensor measurement data.

14. The at least one non-transitory computer readable medium of claim 13, wherein the adjusted confidence value is based at least in part on a correlation between the second sensor measurement data and the event.

15. The at least one non-transitory computer readable medium of claim 13, wherein predicting the occurrence of the event comprises:

inputting the detected gesture and the second sensor measurement data to an event prediction model configured to output indicia of the predicted occurrence of the event.

16. The at least one non-transitory computer readable medium of claim 13, wherein:

the medical device comprises an infusion device; and the automatically configuring of the operation comprises adjusting a delivery control parameter in a manner that is influenced by the adjusted confidence value.

17. The at least one non-transitory computer readable medium of claim 13, wherein the medical device is further configured to maintain the confidence value of the detected gesture based at least on a lack of the corroboration and a lack of the contraindication.

18. A system comprising:
a medical device that regulates delivery of fluid to a patient;
a primary sensor unit associated with a first location on a body of the patient and configured to provide first sensor measurement data corresponding to a physical movement by the patient;
a secondary sensor unit associated with a second location on the body of the patient and configured to provide second sensor measurement data; and
at least one controller configured to detect a gesture of the patient based on the first sensor measurement data; assign a confidence value to the detected gesture based on one or more first gesture features corresponding to at least a portion of the first sensor measurement data; increase the confidence value of the detected gesture based on a temporal consistency between the one or more first gesture features from the first location on the body and one or more second gesture features from the second location on the body corresponding to at least a portion of the second sensor measurement data within a threshold period of time, and corroboration between the one or more first gesture features and the one or more second gesture features, or decrease the confidence value of the detected gestures based on a temporal inconsistency between the one or more first gesture features from the first location on the body and the one or more second gesture features from the second location on the body within the threshold period of time, and contradiction between the one or more first gesture features and the one or more second gesture features; predict an occurrence of an event based on the detected gesture and the increased or decreased confidence value; and configure the medical device to deliver the fluid in a manner that is influenced by the occurrence of the event such that the medical device is configured to increase the delivery of the fluid responsive to the increased confidence value and the corroboration, and decrease the delivery of the fluid responsive to the decreased confidence value and the contradiction.

19. The system of claim 18, wherein the at least one controller is further configured to configure the medical device to maintain the confidence value of the detected gesture based at least on a lack of the corroboration and a lack of the contradiction.

* * * * *